United States Patent [19]
Coates

[11] Patent Number: 5,557,200
[45] Date of Patent: * Sep. 17, 1996

[54] NUCLEAR MAGNETIC RESONANCE DETERMINATION OF PETROPHYSICAL PROPERTIES OF GEOLOGIC STRUCTURES

[75] Inventor: George R. Coates, Austin, Tex.

[73] Assignee: Numar Corporation, Malvern, Pa.

[ * ] Notice: The portion of the term of this patent subsequent to Jun. 15, 2012, has been disclaimed.

[21] Appl. No.: 261,542

[22] Filed: Jun. 17, 1994

Related U.S. Application Data

[63] Continuation-in-part of Ser. No. 898,990, Jun. 15, 1992, Pat. No. 5,412,320, which is a continuation-in-part of Ser. No. 701,516, May 16, 1991, abandoned.

[51] Int. Cl.$^6$ ..................................................... G01V 3/00
[52] U.S. Cl. ........................................... 324/303; 324/300
[58] Field of Search .................................. 324/300, 301, 324/302, 303, 304

[56] References Cited

U.S. PATENT DOCUMENTS

| | | | |
|---|---|---|---|
| 3,213,357 | 10/1965 | Brown et al. | 324/5 |
| 3,508,438 | 4/1970 | Alger et al. | 73/152 |
| 4,291,271 | 9/1981 | Lauffer | 324/307 |
| 4,710,713 | 12/1987 | Strikman | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,933,638 | 6/1990 | Kenyon et al. | 324/303 |
| 5,023,551 | 6/1991 | Kleinberg et al. | 324/303 |
| 5,212,447 | 5/1993 | Paltiel | 324/303 |
| 5,280,243 | 1/1994 | Miller | 324/303 |
| 5,309,098 | 5/1994 | Coates et al. | 324/303 |
| 5,363,041 | 11/1994 | Sezginer | 324/303 |
| 5,432,446 | 7/1995 | MacInnis et al. | 324/303 |

OTHER PUBLICATIONS

C. Clavier et al., "Theoretical and Experimental Bases for the Dual–Water Model for Interpretation of Shaly Sands", *Society of Petroleum Engineers Journal*, Apr. 1984.

George R. Coates and J. L. Dumanoir, "A New Approach to Improved Log–Derived Permeability", SPWLA *Society of Petroleum Engineers* 14th Annual Logging Symposium, 1973.

Herrick, R. C., Couturie, S. H., Best, D. L.; "An Improved Nuclear Magnetism Loggin System and its Application to Formation Evaluation" *Society of Petroleum Engineers of AIME*, 54th Annual Fall Technical Conference and Exhibition, Sep. 23–26, 1979.

Timur, A., "Pulsed Nuclear Magnetic Resonance Studies of Porosity, Movable Fluid, and Permeability of Sandstones", *Society of Petroleum Engineers of AIME*, Journal of Petroleum Technology, Jun. 1969.

H. Y. Carr et al., "Effects of Diffusion on Free Precession in Nuclear Magnetic Resonance Experiments," Phys. Review, vol. 94, No. 3, pp. 630–638, May 1954.

G. R. Coates et al., "The MRIL in Conoco 33–1: An Investigation of a New Magnetic Resonance Imaging Log," paper DD, 32nd Annual Logging Symposium of the Society of Professional Well Log Analysts (SPWLA), Midland, TX, Jun. 1991.

(List continued on next page.)

*Primary Examiner*—Sandra L. O'Shea
*Assistant Examiner*—Mack Haynes
*Attorney, Agent, or Firm*—Pennie & Edmonds

[57] ABSTRACT

An improved system for using magnetic resonance techniques to obtain information relating to geologic structures is disclosed. The system of the present invention uses values of the total porosity of a formation and the porosity obtained via NMR pulse echo techniques to derive additional information relating to the underlying geologic structures, including resistivity and water saturation. Independent estimate is provided to account for the presence of clay mineral content.

3 Claims, 32 Drawing Sheets

OTHER PUBLICATIONS

G. R. Coates et al., "Core Data and the MRIL Show: A new Approach to 'Formation Factor', "33rd Annual Logging symposium of the SPWLA, Oklahoma City, OK, Jun. 1992.

J. Howard et al., "Proton Magnetic Resonance and Pore Size Variations in Reservoir Sandstones," SPE 20600, 65 Annual Technical Conference and Exhibition of the Society of Petroleum Engineers (SPE), New Orleans, LA, Sep. 1990.

W. E, Kenyon et al., "Pore–size Distribution and NMR in Microporous Cherty Sandstones," Paper LL, 30th Annual Logging Symposium of SPWLA, Jun. 1989

M. N. Miller et al., "Spin Echo Magnetic Resonance Logging: Porosity and Free Fluid Index Determination," SPE 20561, 65th Annual Technical Conference and Exhibition of the Society of Petroleum Engineers, New Orleans, LA, Sep. 1990.

C. E. Morriss et al., "Field Test of an Experimental Pulsed Nuclear Magnetism Tool," paper GGG, 34th Annual Logging Symposium of SPWLA, Calgary, Alberta, Jun. 1993.

M. H. Waxman et al., "Electrical Conductivities in Oil–Bearing Shaly Sands," SPE Journ. 8, Jun. 1968.

Kleinberg et al., "Novel NMR Apparatus for investigating an External Sample," Journal of Magnetic Resonance 97, pp. 466–485 (1992).

W. E. Kenyon, "Nuclear Magnetic Resonance as a Petrophysical Measurement," Nucl. Geophys. vol. 6, No. 2, pp. 153–171, 1992.

G. R. Coates et al., "Restrictive Diffusion From Uniform Gradient NMR Well Logging," SPE 26472, 68th Annual Technical Conference and Exhibition of the Society of Petroleum Engineers, Houston, TX, Oct. 1993.

NUCLEAR MAGNETIC RESONANCE DETERMINATION OF PETROPHYSICAL PROPERTIES OF GEOLOGIC STRUCTURES

CONTINUING APPLICATION DATA

This application is a continuation-in-part of application Ser. No. 07/898,990, filed Jun. 15, 1992, now U.S. Pat. No. 5,412,320, which is a continuation-in-part of application Ser. No. 07/701,516, filed May 16, 1991, now abandoned.

FIELD OF INVENTION

The present invention relates to systems for obtaining quantitative and qualitative measurements of geologic structures. More specifically, the present invention provides an efficient and effective method for using information obtained via nuclear magnetic resonance (NMR) techniques to determine petrophysical properties of geologic structures.

BACKGROUND

A key petrophysical property in determining whether a formation will produce viable amounts of hydrocarbons is the water saturation, $S_w$, of the formation. $S_w$ is defined as the percentage pore space of the formation that is filled with formation water and is related to other parameters of interest, such as the bulk-volume water (BVW), the bulk-volume hydrocarbon (BVH) and the porosity (PHI) of the formation as follows:

$$BVW = PHI * S_w;$$

$$BVH = PHI * (1 - S_w).$$

Obviously, if the formation's pore space is completely filled with water, that is if $S_w = 100\%$, such a formation is of no interest for the purposes of an oil search. On the other hand, if the formation is at the minimum possible water saturation it will produce all hydrocarbons and no water. The minimum possible water saturation of a formation is known as irreducible water saturation, $S_{WIRR}$.

The irreducible water saturation $S_{WIRR}$ is related to the average grain size of a formation. For example, shales and clays, due to their platy structure and small grain size have immense surface areas compared to the same volume of sand grains. The effect of this is to bind large quantities of water to their structure. Additionally, due to their fine grain size and the strong forces that hold the water in place, shales have essentially zero permeability and high porosity. Thus, shales decrease the porosity of the formation that is available to hold producible (free) fluids and increase the amount of water that is bound to the formation. Using the relationship above, the irreducible water saturation $S_{WIRR}$ allows one to compute the water bound to the formation, known as the bulk-volume irreducible water (BVI) of the formation, i.e., the percentage of the unit volume of the formation that is irreducible formation water, as follows:

$$BVI = PHI * S_{WIRR}.$$

Given the critical importance of the water saturation as discussed above, many techniques have been proposed for determining its value for a given formation. The standard approach to obtaining a value for $S_w$ is through the Archie formation factor process. The formation factor F is defined as:

$$F = R_o/R_w = C_w/C_o,$$

where $R_o$ is the resistivity of a reservoir rock when fully saturated with aqueous electrolyte of resistivity $R_w$, and $C_o$ and $C_w$ are corresponding conductivities. Further, given knowledge of porosity (PHI), which is the fraction of the total volume of a sample that is occupied by pores and voids; and resistivity ($R_t$), i.e., the resistance of reservoir rock that is partially saturated to degree $S_w$ with electrolyte of resistance $R_o$, via conventional logging techniques, Archie formation factor analysis provides the following empirical relationships which relate the porosity (PHI) to formation factor (F), and resistivity to saturation. The relationships are:

$$F = \frac{a}{PHI^m} \qquad (1)$$

and $$S_w^n = \frac{F R_W}{R_t}$$

In practice, the values of "a" (formation-factor coefficient), "m" (cementation exponent), and "n" (saturation exponent) vary with the type of formation and the nature of the hydrocarbon. However, in most cases an analyst will use the same relationship over large intervals, intervals that may include a variety of lithologies, pore types, and grain sizes. In such circumstances, it is often difficult to select the correct values of "a", "m", and "n". A selection of the correct values is of a significant concern since these parameters are used to relate porosity to formation factor F, and, in conjunction with resistivity, to saturation.

In an attempt to reduce the complexity of the above-mentioned relationships, it is has been observed that if "a" is a constant, it should equal to 1, since F must be equal to 1.0. in 100% porosity. Thus, the relationship between formation factor F and porosity reduces to:

$$F = \frac{1}{PHI^m}$$

Further simplification of Eq. (1) is possible if the porosity PHI and the saturation $S_W$ are not treated as independent variables. While the assumption that porosity and saturation are independent has been useful for performing laboratory studies of geologic structures, as known to log analysts, this complexity of the model is not necessary for interpreting an actual resistivity log.

Considering the above, it has been proposed to eliminate porosity and saturation as independent variables and use only the bulk-volume water term (the product of porosity and saturation) to model the relationship between the conductivity of the fluids involved and the measured conductivity of the formation. This approach has the additional benefit of avoiding the need to independently estimate the numerical values for the exponents "m" and "n."

In an article by George R. Coates and J. L. Dumanoir, entitled "A New Approach to Improved Log-Derived Permeability," SPWLA, Fourteenth Annual Logging Symposium, p. 1, 1973, it was found that a common value, "w", could be adopted for both the saturation exponent, "n", and cementation exponent, "m". The proposed single exponent expression used to relate BVW, i.e., $PHI * S_w$, to resistivity is:

$$(PHI * S_w)^w = R_w/R_t$$

where:

w is the single exponent used to relate the BVW to $R_w/R_t$;

PHI is the total porosity of the rock;

$R_w$ is the resistivity of the formation water; and $R_t$ is the true resistivity of the rock.

The proposed single exponent expression has not been widely used in the logging industry until recently because a log analyst could only assume a rock to be completely water filled in order to examine an apparent value for w. In other words, the single exponent equation could only be solved for w by assuming that PHI*$S_w$=PHI. The porosity term was determinable via conventional logging instruments.

The results obtained by assuming a water filled condition were only valid in the water zones and resulted in an overestimation of w in the hydrocarbon zones of interest. It has long been desired to solve w for a hydrocarbon filled condition, i.e., PHI*$S_w$=BVI, such that a valid result for w could be obtained for hydrocarbon zones of interest.

Additional complications in using Eq. (1) to obtain accurate values for the desired parameters arise from the fact that the resistivity measurements are affected by the presence of clay minerals in the formation. In order to compensate for these effects which may significantly reduce the accuracy of the measurements it is required to obtain an estimate of the clay minerals content of the formation. Such estimates are traditionally obtained using subjective, frequently complicated and inaccurate clay indicator methods.

With the advent of NMR logging, new options for determining w as well as other fluid flow properties of porous media have arisen. In an article by A. Timur, entitled "Pulsed Nuclear Magnetic Resonance Studies of Porosity, Movable Fluid, and Permeability of Sandstones," in the Journal of Petroleum Technology, June 1969, page 775, it was shown experimentally that NMR methods provide a rapid non-destructive determination of porosity, movable fluid, and permeability of rock formation.

It is known that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter T1, known as the spin-lattice relaxation time.

It has been observed that the mechanism which determines the value of T1 depends on molecular dynamics. In liquids, molecular dynamics are a function of molecular size and inter-molecular interactions. Therefore, water and different types of oil have different T1 values.

In the heterogeneous media, such as a porous solid which contains liquid in its pores, the dynamics of the molecules close to the solid surface are also significant and differ from the dynamics of the bulk liquid. It may thus be appreciated that the T1 parameter provides valuable information relating to well logging parameters.

There exist a number of techniques for disturbing the equilibrium of an assembly of magnetic moments, such as those of hydrogen nuclei, for T1 parameter measurements. Each of these techniques provides means for measuring T1 of a rock formation within a certain volume (called the "sensitive volume") which is determined mainly by the shape of the magnetic field surrounding the magnetic structure. The signal-to-noise ratio of the measurement is limited by the ratio of the sensitive volume to the uniformity of the magnetic field within said volume (maximum flux density minus minimum flux density), and increases in proportion to this ratio.

In any given NMR instrument configuration, the apparatus will respond only to nuclei residing within the sensitive volume. In the present invention and prior art instruments described herein, the boundaries of the sensitive volume are determined by radiation patterns of transmitting and receiving antennae as well as a combination of the detailed structure of the magnetic field with the receiver's frequency passband. The radio frequency that a given nucleus will respond to or emit when excited is proportional to the flux density of the magnetic field in which it is immersed. The proportionality factor depends upon the nuclear species. For hydrogen nuclei, that factor is 42.5759 MHz/Tesla. If the NMR receiver's passband extends from 1.30 MHz to 1.31 MHz, the instrument will be sensitive to hydrogen nuclei in regions of the magnetic field that have flux densities between 30.5 mT and 30.8 mT, providing the antenna radiation pattern allows receiving sufficient signal from that locations.

If it is desired to study nuclei located within a particular region, the magnetic field structure, antenna radiation pattern and receiver passband must all be adjusted to be sensitive to that and only that region. Since the signal-to-noise ratio of the resulting signal is proportional to (among other factors) the square root of the receiver passband width, it is important to minimize the variation of the magnetic field within the desired sensitive volume; smaller variations (better field uniformity) mean a better signal-to-noise ratio. Since the signal-to-noise ratio also increases with increasing frequency, the nominal magnetic field intensity within the volume is also very important. It is immaterial whether this nominal intensity is defined as the central value, average value or some other value within the range of values encompassed by the sensitive volume because only large differences in signal-to-noise ratio are significant.

One technique for measuring T1 of a rock formation is exemplified by what is known as the "Schlumberger Nuclear Magnetic Logging Tool." That tool is described by R. C. Herrick, S. H. Couturie, and D. L. Best in "An Improved Nuclear Magnetic Logging System and Its Application to Formation Evaluation," SPE8361 presented at the 54th Annual Fall Technical Conference and Exhibition of the Society of Petroleum Engineers of AIME, held in Las Vegas, Nev., Sep. 23–26, 1979, and also by R. J. S. Brown et al. in U.S. Pat. No. 3,213,357 entitled "Earth Formation and Fluid Material Investigation by Nuclear Magnetic Relaxation Rate Determination."

The Schlumberger Nuclear Magnetic Logging Tool measures the free precession of proton nuclear magnetic moments in the earth's magnetic field by applying a relatively strong DC polarizing field to the surrounding rock formation in order to align proton spins approximately perpendicularly to the earth's magnetic field. The polarizing field must be applied for a period roughly five times T1 (the spin-lattice relaxation time) for sufficient polarization (approximately two seconds). At the end of polarization, the field is turned off rapidly. Since the protons spins are unable to follow this sudden change, they are left aligned perpendicularly to the earth's magnetic field and precess about this field at the "Larmor Frequency" corresponding to the local earth's magnetic field (roughly from 1300 to 2600 Hz, depending on location).

The spin precession induces in a pick-up coil a sinusoidal signal whose amplitude is proportional to the density of protons present in the formation. The signal decays with a time contrast "T2" (transverse relaxation time) due to non-homogeneities in the local magnetic field over the sensing volume.

Improved NMR logging tools and methods for using these tools are described generally in U.S. Pat. Nos. 4,710,713;

4,717,876; 4,717,877; 4,717,878; 5,212,447 and 5,280,243 all of which are commonly owned by the assignee of the present invention.

The method of the present invention, described in greater detail below, uses the logging tools and techniques described in the above referenced patents to obtain previously unavailable data relating to the composition of a geologic structure. The measurements from the above described tools are used in combination with new and existing theoretical developments to obtain enhanced information regarding the petrophysical properties of geologic structures. In particular, a novel interpretation of standard and NMR measurements is used to obtain characteristics of the formation including its clay mineral content which may then be used to determine key petrophysical parameters such as the water saturation.

SUMMARY OF THE INVENTION

The method of the present invention provides an improved system for using NMR techniques for obtaining information relating to geologic structures. In the system of the present invention, a NMR logging tool is used to impart magnetic polarization fields on a portion of a geologic formation. Nuclear magnetic resonance signals from the excited nuclei in the formation are then detected to obtain data for calculating a number of important petrophysical parameters including the porosity, the clay mineral content and the bulk volume irreducible water of the formation.

The system and method of the present invention provide the capability of directly measuring the volume of irreducible water (BVI) which measurement is used to improve the reliability of log derived water saturations, especially in complex lithologies. In addition, observations of the porosity response of the magnetic resonance log (MRL) in comparison with other porosity measurements provide a more direct method for determining the clay mineral bound water content than is generally available from conventional log data.

Specifically, due to the fact that the NMR tool is blind to relaxation times shorter than about 1.5 ms which are indicative of clay mineral bound water and other pore systems with short relaxation properties, in accordance with the present invention the MRL, operated at about 2 ms pulse rate, measures porosity that can be used as an estimate of the effective pore space of the formation, excluding the effects of the clay porosity. Thus, the effective porosity ($PHI_{ef}$) is related to the total porosity ($PHI_T$) and the clay bound water porosity ($PHI_{cl}$) as follows:

$$PHI_{MRL}=PHI_{EF}=PHI_T-PHI_{CL},$$

where $PHI_{MRL}$ is the MRL measured porosity.

In accordance with a preferred embodiment of the present invention, this relationship provides the capability to determine the clay mineral bound water fraction (Swb) directly when the MRL porosity measurement is combined with an estimate of the total porosity obtained from conventional sources. This feature in turn allows the user to make corrections in the resistivity log measurements and thus obtain accurate water saturation estimates.

In a different embodiment, the porosity and the bound volume irreducible water are further used to determine additional petrophysical properties of the formation. In particular, the bulk volume water is calculated using the expression:

$$(PHI*S_w)^w=R_w/R_t$$

for a first apparent w by assuming a water filled formation ($PHI*S_W=PHI$) and for a second apparent w by assuming an oil filed formation ($PHI*S_W=BVI$). Additional petrophysical parameters such as the irreducible saturation profile of the formation are derived from a new model relating the w parameter to the two apparent values of w.

BRIEF DESCRIPTION OF THE DRAWINGS

FIG. 24 B is a Pickett plot of clay rich shales using Density-Neutron crossplot porosity.

FIG. 24 C is a picket plot of clay rich shales using density porosity (Sandstone Matrix).

FIG. 25 B is a Density-Neutron plot with clay rich shale highlighted.

FIG. 26 B is a Density-Neutron plot with total porosity scaling.

DETAILED DESCRIPTION OF THE PREFERRED EMBODIMENT

Figure 1:
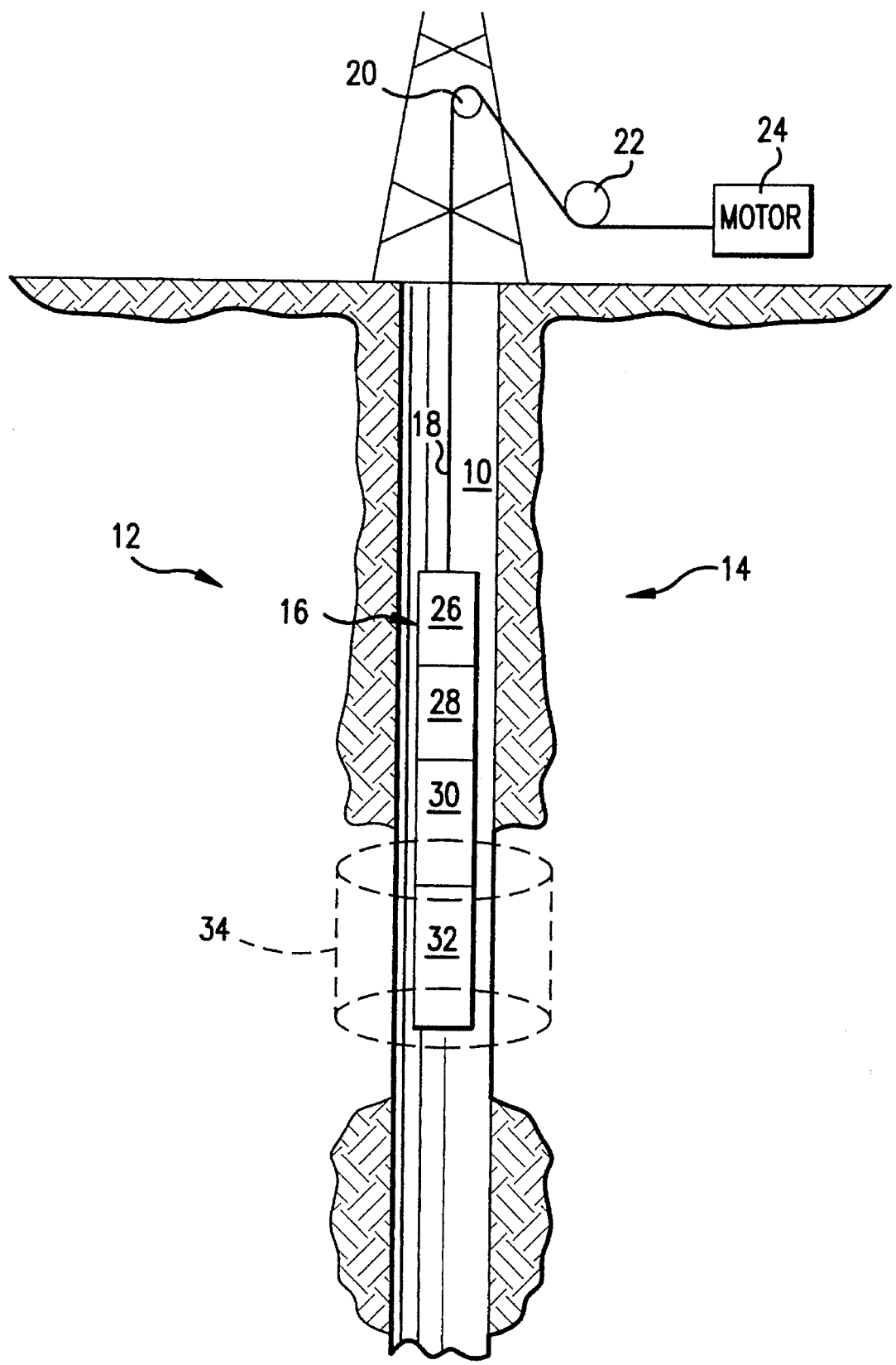
FIG. 1 is a partially pictorial, partially block diagram illustration of a well logging apparatus for obtaining nuclear magnetic resonance measurements of a geologic structure.

Referring to FIG. 1, a borehole 10 is shown in formation 12 having structures to be examined using the method and apparatus of the present invention. Within the borehole, there is a logging tool 16 which is suspended by a cable 18 routed over pulleys 20 and 22, with the position of the cable 18 being determined by a motor 24.

The upper portion of the logging tool 16 comprises telemetry electronics 26, gamma ray sensing electronics 28 and magnetic resonance imaging (MRI) electronics 30. A MRI probe 32 is suspended at the bottom of the probe to provide excitation to the surrounding geologic formation. The excitation field has a generally cylindrical shape as represented by reference numeral 34. Improved devices which can be used for the probe 32 are described generally in U.S. Pat. Nos. 4,710,713; 4,717,876; 4,717,877; and 4,717,878, 5,212,447 and 5,280,243 which, by this reference, are incorporated herein for all purposes.

The spin-spin pulse-echo measurement of the spin-echo relaxation of the sample, in a homogenous isotropic media, reflects the surface-to-volume characteristics of the pores. In typical rocks encountered in the well-logging environment, the rocks are complex mixtures of minerals which often include a variety of pore sizes. Consequently, the measured spin-echo relaxation in such an environment is a complex phenomenon, a reflection of the variations which exist in terms of pore surface-to-volume ratios and surface-to-fluid interactions.

Figure 2A:
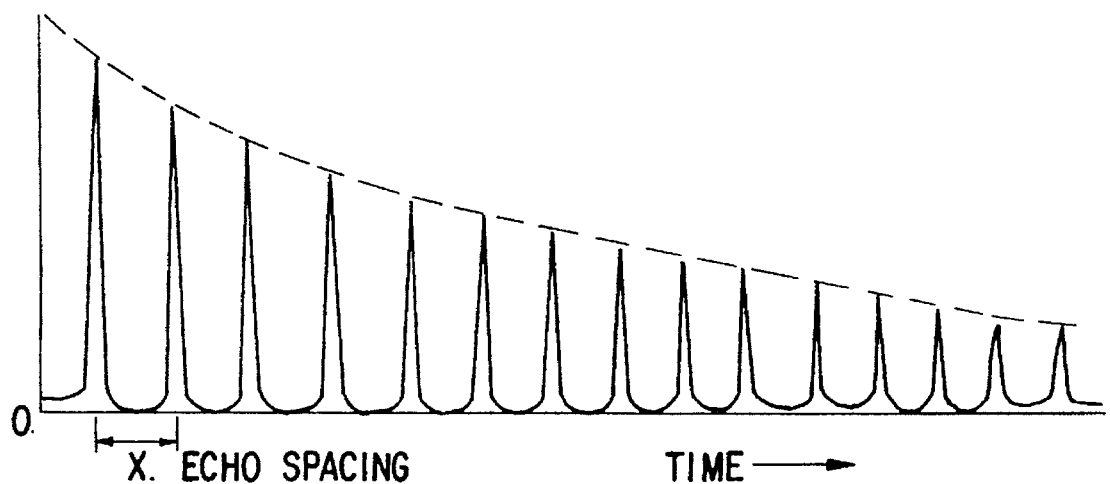
FIG. 2 is a graphical illustration of a chain of spin-echo relaxation signals as a function of amplitude versus time for a geologic structure investigated using a nuclear magnetic resonance system such as that shown in FIG. 1.
Figure 2B:
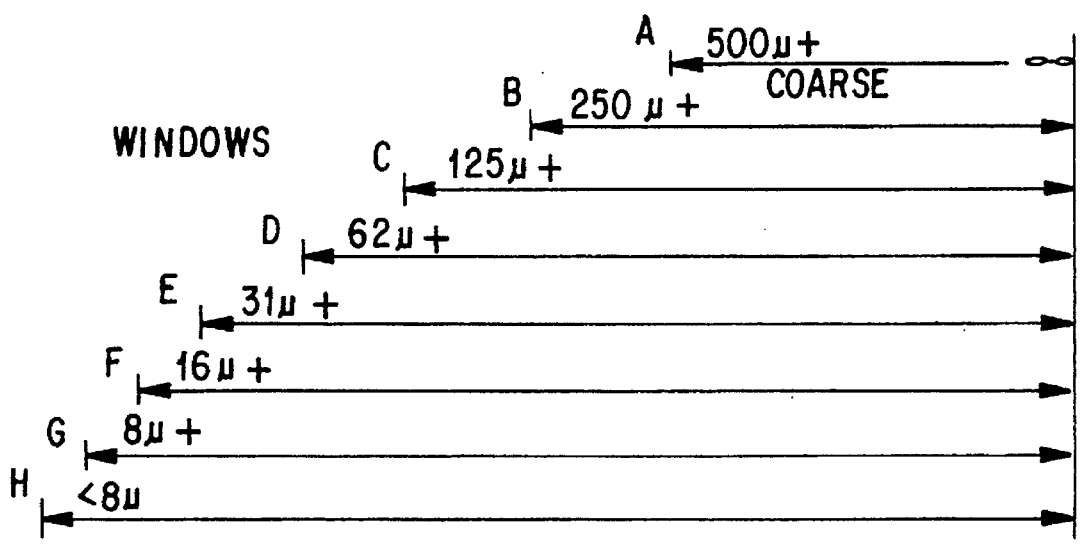

FIG. 2 is a graphical illustration of a chain of spin-echo relaxation signals as a function of amplitude versus time for a geologic structure investigated using a nuclear magnetic resonance system such as that shown in FIG. 1. The spacing of the time intervals between the pulses in this application is typically between 1.5 and 3 milliseconds. The time intervals labelled "A–H" correspond to the signal intervals for various particle sizes, with interval "A" corresponding to the interval for particles larger than 500 μm and interval "H" corresponding to the interval for particles of larger than 8 μm, etc.

Using the echoes in each time window to regress to time zero establishes an apparent porosity amplitude. Such regression techniques are known to those skilled in the art and are described in the following references: K. Fukunaga, *Introduction to Statistical Pattern Recognition*, Academic Press, 1972; Bhattacharyya & Johnson, *Statistical Concepts and Methods*, Wiley & Sons, 1977; and Devijver & Kittler, *Pattern Recognition—A Statistical Approach*, Prentice Hall, 1982.

As a consequence of the actual tool operation, the measurement of spin-echo information is delayed for a few milli-seconds (typically <5 m secs for the tools described in the above referenced patents incorporated herein by reference). During this period of time ($t_{del}$) no formation information is uniquely measured. This $t_{del}$ time period includes the surface-to-volume response associated with a select pore-size group that is directly linked with the pore-sizes related to clay size grains. Thus, by proper selection of the echo windows through use of the $t_{del}$ parameter, a spin-echo measurement can be provided which measures the total pore-space minus those associated with the particular pore surface-to-volume ratios related to the noted particle sizes.

The pore surface-to-volume responses that are missed during this $t_{del}$ period include the clay mineral fraction of the rock-space, thus providing a direct link between such a NMR measured porosity and the total porosity of the rock. In other words, in a clay mineral free environment, with pores >2 μm, extrapolation of the NMR echo signals to time zero provides a measure of the total porosity $PHI_t$ but, in a shaly-sand that contains clay minerals and thus clay size pores, the NMR porosity measurement does not take into account the influence of the non-reservoir quality micropores. As described in more detail below, this feature makes the NMR porosity measurement particularly useful in assessing the reservoir's capacity to support production.

Prior art references discussed above (see, for example, A. Timur, *Journal of Petroleum Technology* article) show that NMR may be used for the determination of a rock parameter called the free-fluid index (FFI). The FFI method relies on use of relaxations which occur during a late measurement time following a select $t_{del}$. This time period being referred to as the long component of the relaxation phenomenon (typically $t_{del}$'s $\geq$22 m secs). The difference between the pore space described as the long component relaxation and that provided by the full NMR spectrum provides a direct measure of the pore bulk-volume that is held in place by existing surface tension and other capillary forces. This parameter, the bulk-volume of irreducible water, is directly related to pore surface-to-volume of the non-clay size rock.

In the above-mentioned U.S. Ser. No. 07/701,516, filed May 16, 1991, the content of which is expressly incorporated herein by reference thereto, the NMR measurement of porosity and bulk-volume irreducible are in turn used to find the intrinsic permeability of the rock, since these measured parameters (porosity and bulk-volume irreducible) reflect the principle component of the rock's producibility, through a model such as that of the Coates' free-fluid perm model.

The method and apparatus of the present invention is based on the discovery that NMR values of porosity and bulk-volume irreducible water can be further used to determine the exponential relationship "w" between the bulk-volume water (BVW=PHI*$S_w$) of the formation and the resistivity ratio $R_w/R_t$ through the equation:

$$(PHI*S_w)^w = R_w/R_t \qquad (2)$$

where:

w is the single exponent used to relate the BVW to $R_w/R_t$;
PHI is the rock's total porosity;

$R_w$ is the resistivity of the formation water; and $R_t$ is the rock's true resistivity.

As discussed above, prior art methods could only solve for an apparent w by assuming a water filled condition (PHI*$S_w$=PHI), since prior art devices could measure porosity but not bulk volume irreducible. This resulted in an overestimation of w in hydrocarbon zones. Advantageously, by knowing NMR bulk volume irreducible water (BVI), a second apparent w can be solved for by assuming a hydrocarbon filled formation (PHI*$S_w$=BVI). Thus, the present invention provides accurate values for w for water filled formation as well as for hydrocarbon filled formations.

The apparent values of w are solved for by making two assumptions: First, the zones of the formation are at irreducible water saturation ($S_w$=$S_{WIRR}$, BVW=BVI, w=wi), and second, that the zones are water filled ($S_w$=1.0, BVW= PHI, w=ww). Solving Equation (2) for the apparent w's at these two endpoints yields:

$$wi = \log(R_w/R_t)/\log(BVI) \quad (3)$$

$$ww = \log(R_w/R_t)/\log(PHI) \quad (4)$$

Therefore, since $R_t$ is determinable via a conventional resistivity log as is known in the art, and since BVI and PHI for a given formation are determinable via the NMR devices as described above, once $R_w$ is known, w can be solved for at its two end points, wi and ww.

For typical high porosity shaly sands of the Gulf Coast of the United States, a Pickett Plot has been found useful by those skilled in the art for determining $R_w$. Once $R_w$ is determined via the Pickett Plot, it should be corrected for the effects of clay. Clay correction is also known by those skilled in the art and can be accomplished by using a multiple clay indicator sorting to determine the appropriate clay bound water fraction.

Figure 3:
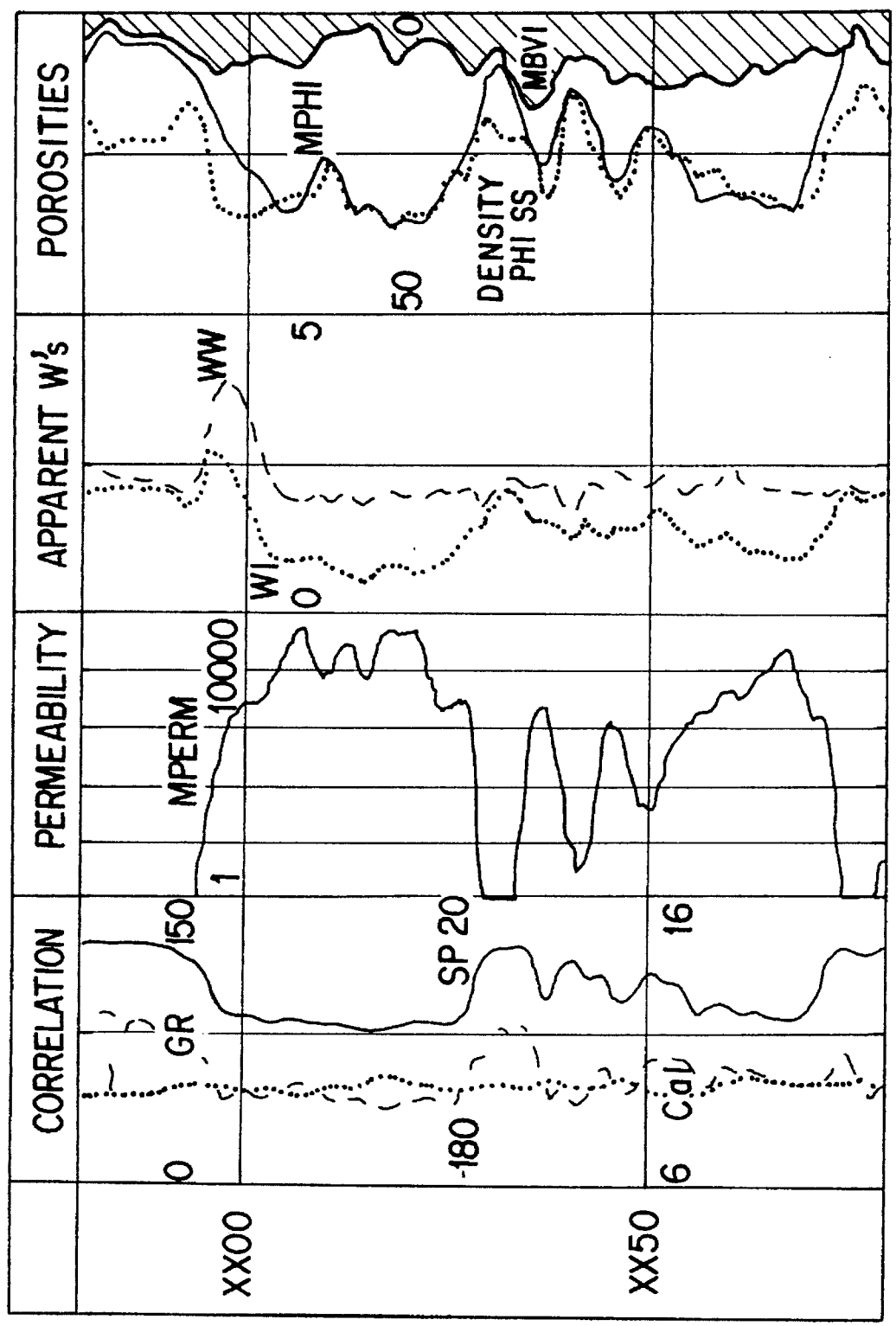
FIG. 3 is a log of typical high porosity sands of the Gulf Coast of the United States and includes the formation's apparent values for w (track 3) and NMR porosity and bulk volume irreducible water (track 4)

Having determined a clay corrected value for $R_w$, the apparent values for w can be ascertained by substituting the NMR measured values for BVI and PHI into Equations (3) and (4), respectively. A log of ww and wi for the above-described Gulf Coast formation can be observed in track 3 of FIG. 3. As expected, when PHI approaches BVI, the two estimates of w tend to approach similar values.

Having determined the apparent values of w, confirmation as to whether these values yield accurate results for the assumed conditions can be ascertained using conventional log interpretation means. Such means will assist in determining whether a particular zone of investigation is likely to be water filled or at irreducible water.

One means for accomplishing this is by plotting ww and wi each separately against a variable strongly linked to saturation, but one that is largely free of formation factor influence, such as the ratio $R_{xo}/R_t$ (where $R_{xo}$ is the flushed zone resistivity). Examples of such plots for ww and wi derived from the above-mentioned high porosity shaly sands of the Gulf Coast of the United States are shown in FIGS. 4 and 5, respectively.

Figure 4:
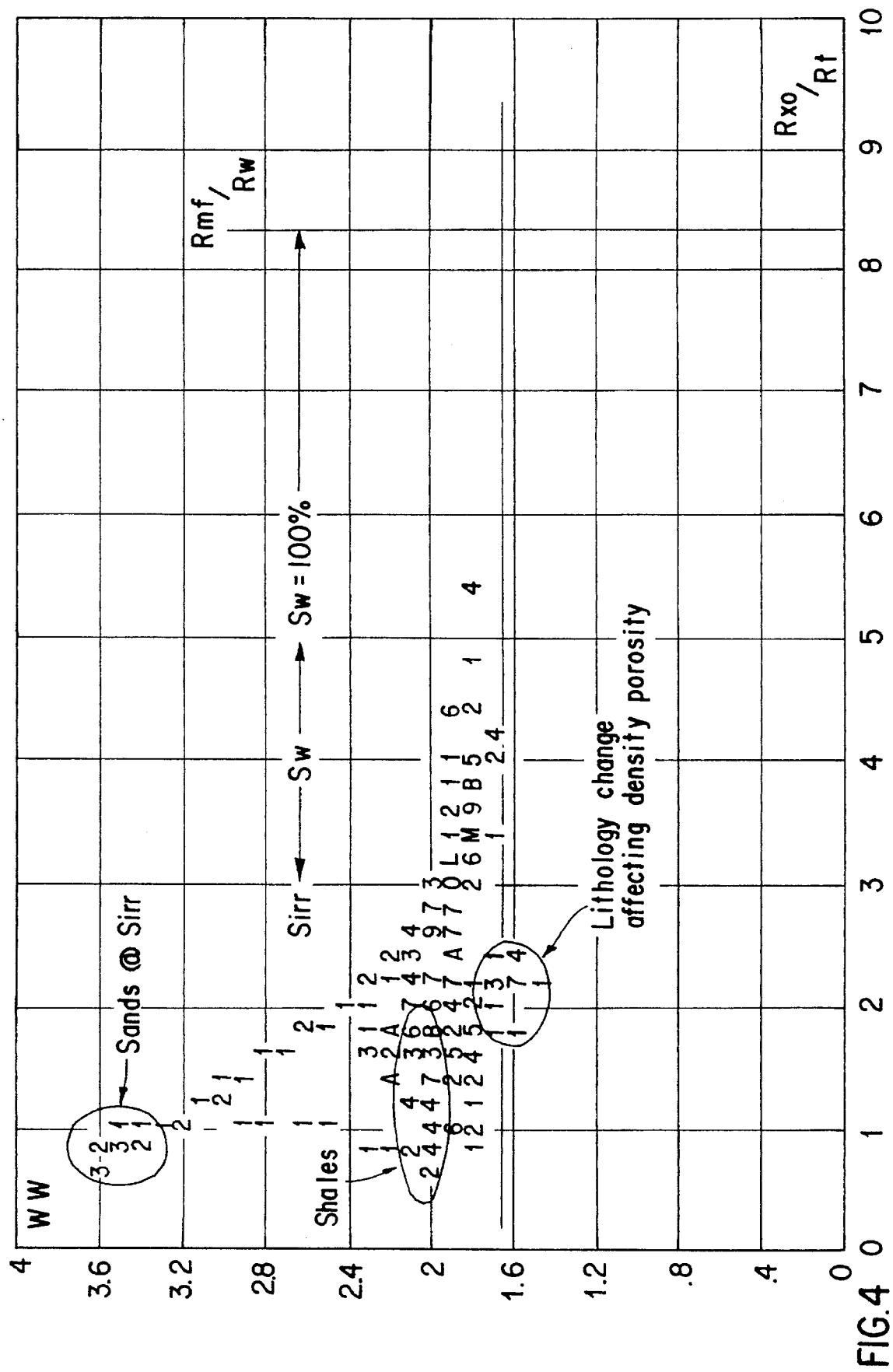
FIG. 4 is a comparison of ww and $R_{xo}/R_t$ for the formation of FIG. 3.

With respect to FIG. 4, several textural conditions should be identifiable to a skilled log analyst and include: sands at irreducible, sands approaching $S_w$=1, shaly sections, a mineral change and trends reflecting the effects of clay minerals and hydrocarbon content. Of particular importance, in water sands, at or near the assumed condition, i.e., $S_w$=1, ww approaches a value of 1.8. This value corresponds well to values often observed in lab studies of similar rocks. Thus, ww provides an accurate determination of w as we approach the assumed condition of PHI*$S_w$=PHI.

Figure 5:
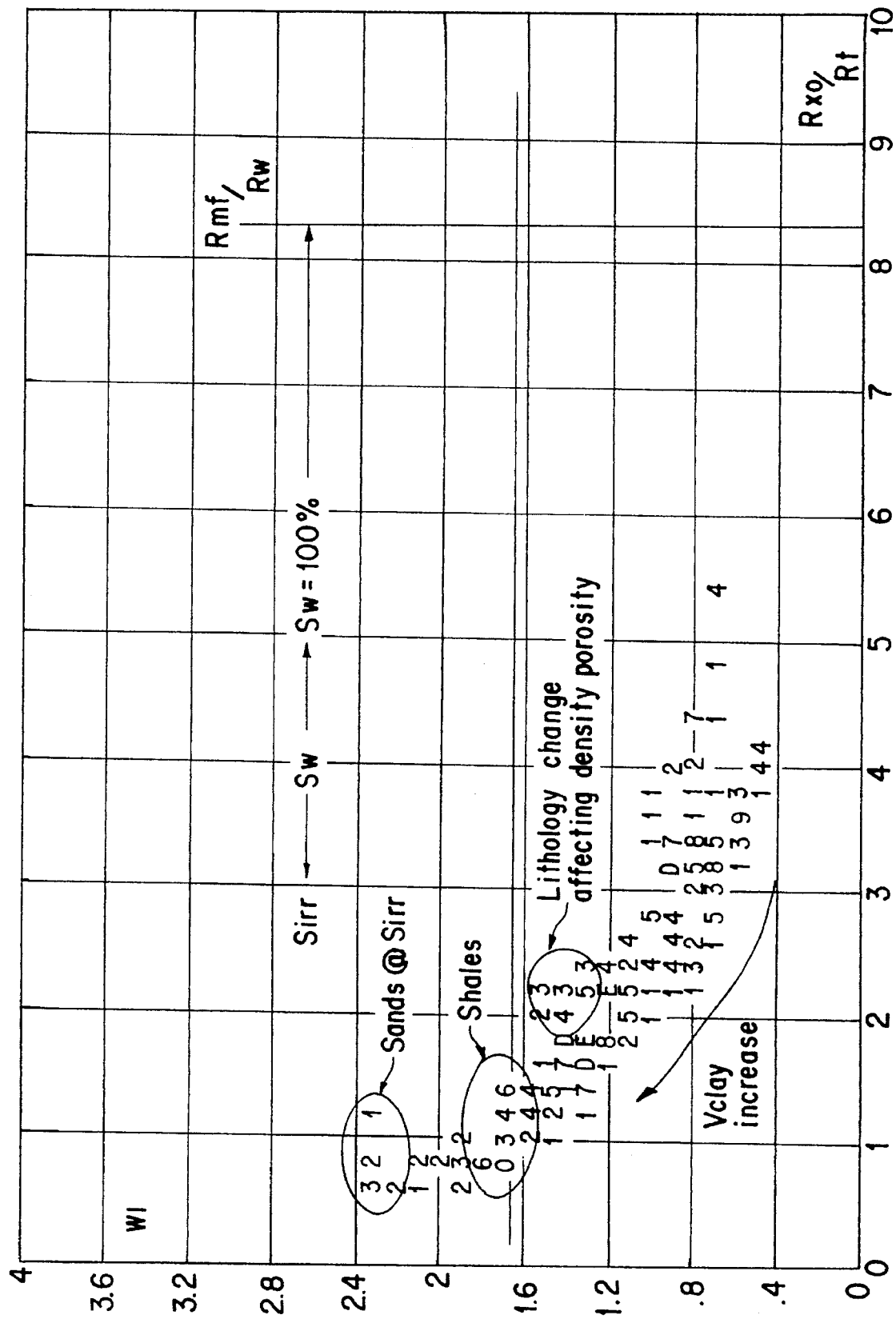
FIG. 5 is a comparison of wi and $R_{xo}/R_t$ for the formation of FIG. 3.

With respect to FIG. 5, the wi plot illustrates the changes in data patterns associated with the change in assumption. Now the sands that are high in hydrocarbon content give values more in line with values observed in laboratory studies for similar rock, while the non-irreducible areas give values much lower. Thus, wi provides an accurate determination of w as we approach the assumed condition of PHI*$S_w$=BVI.

Furthermore, of particular importance is the observation from FIGS. 4 and 5 that w apparently varies with irreducible water saturation. As shown in FIG. 5, as wi decreases, $S_w$ increases. This means the prior art use of constant values for "m" and "n" in both water and hydrocarbon zones may lead to error, since it results in over estimating hydrocarbon content in some formations while underestimating them in others.

Figure 6:
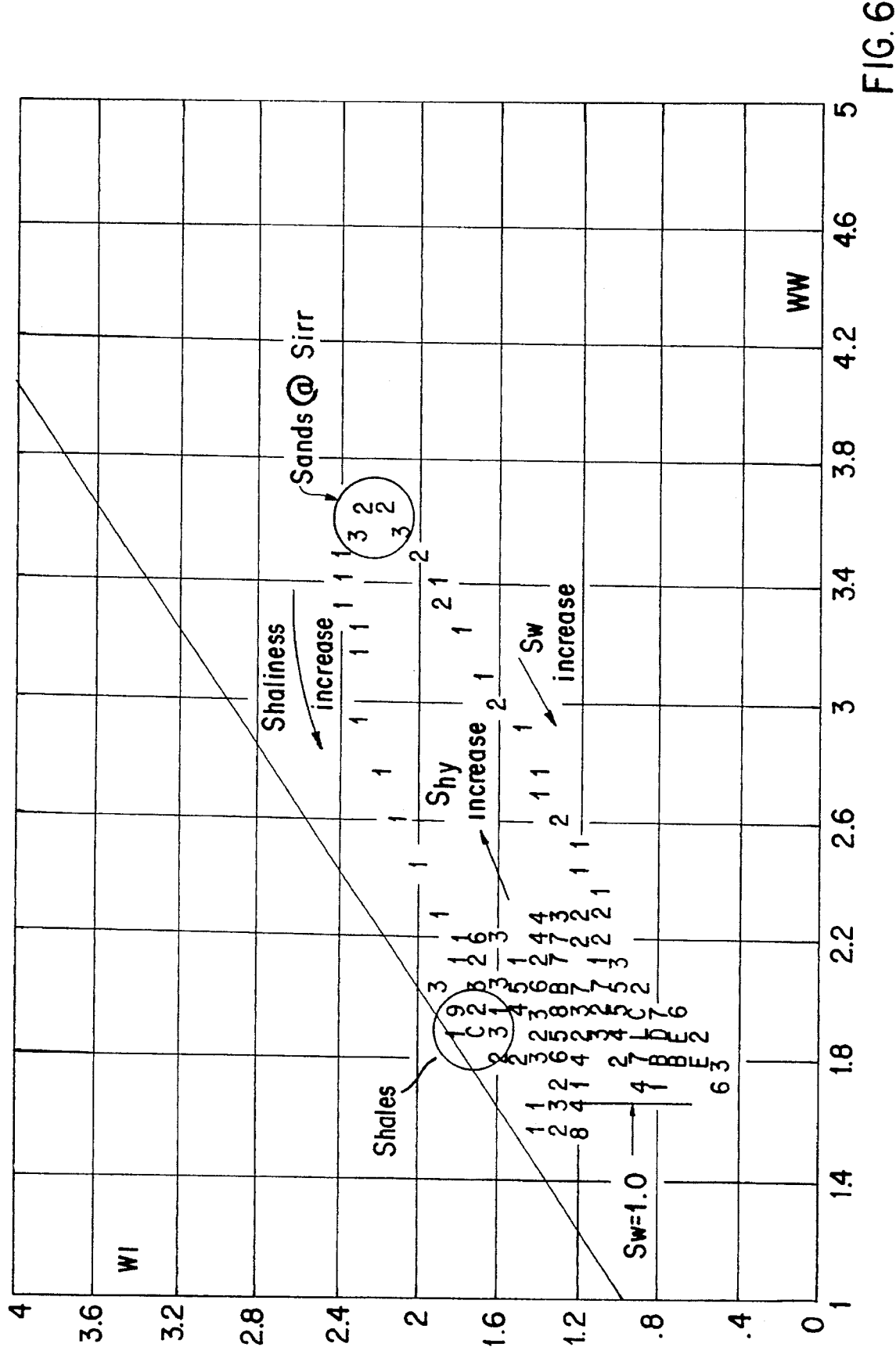
FIG. 6 is a comparison of ww and wi for the formation of FIG. 3.

This trend is further explored in FIG. 6, a plot of wi against ww. Examining FIG. 6, it can be observed by one skilled in that art that water bearing sands are a vertical trend at a value near 1.8, while the sands at $S_{WIRR}$ trend to the right and above this same value.

Figure 7:
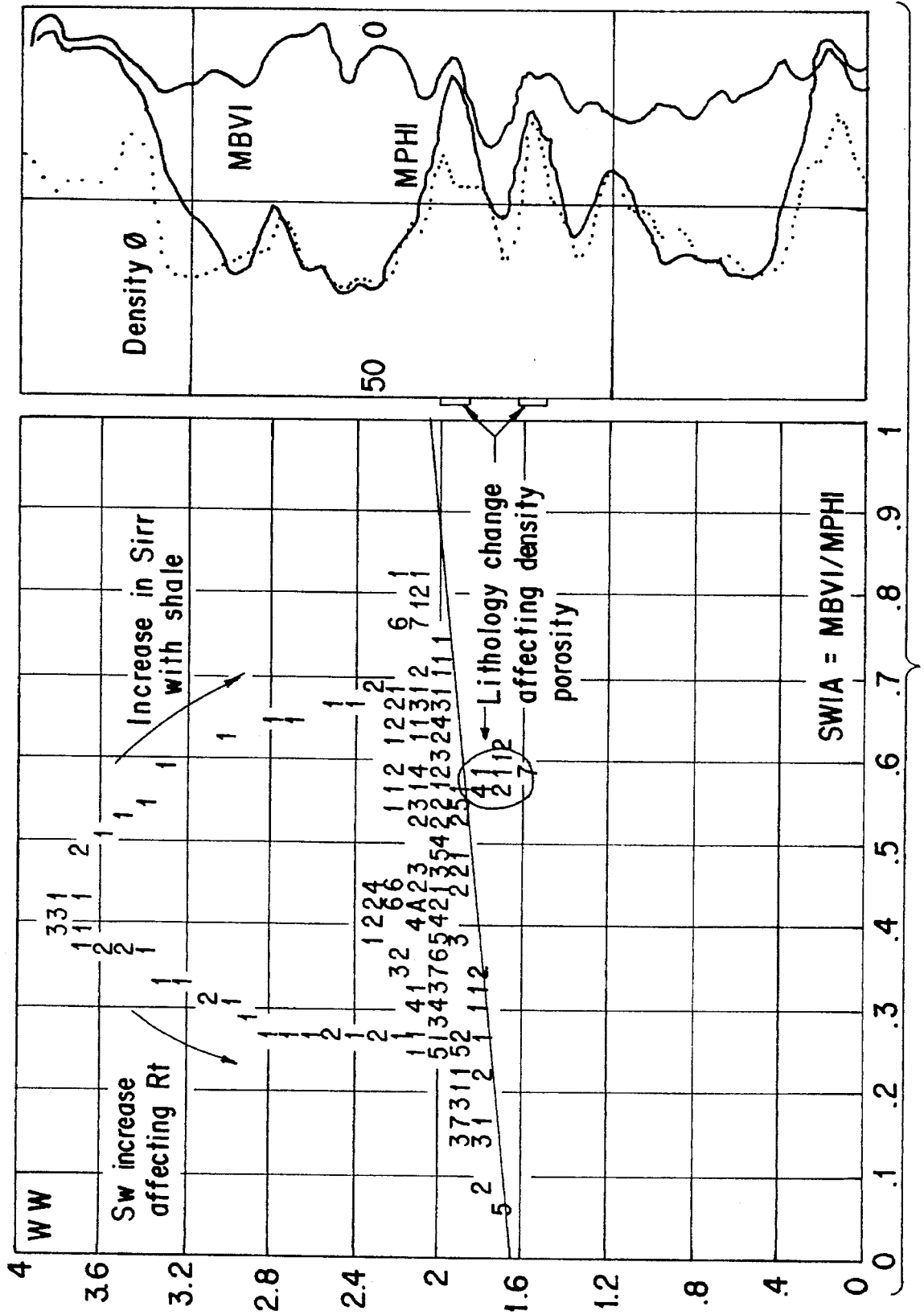
FIG. 7 is a comparison of ww and $S_{WIRR}$ (determined from NMR measurements of bulk-volume irreducible water and porosity) for the formation of FIG. 3.

Further confirmation of w's variation with irreducible water saturation is ascertained from FIG. 7, a plot of ww against the apparent $S_{WIRR}$, where the apparent $S_{WIRR}$ is equivalent to the NMR measured bulk volume irreducible water BVI divided by the NMR measured porosity PHI. FIG. 7 makes it possible to discern trends associated with the effects of increasing $S_w$ as well as trends of increasing $S_{WIRR}$. Importantly, a trend between $S_{WIRR}$ and w is also shown, providing a pattern to develop a relationship for predicting the value of w to use in a shaly sand formation like these. Determining the best-fit first order equation from the trend depicted in FIG. 7 results in the following equation:

$$w = 0.4*S_{WIRR} + 1.65 \quad (5)$$

Figure 8:
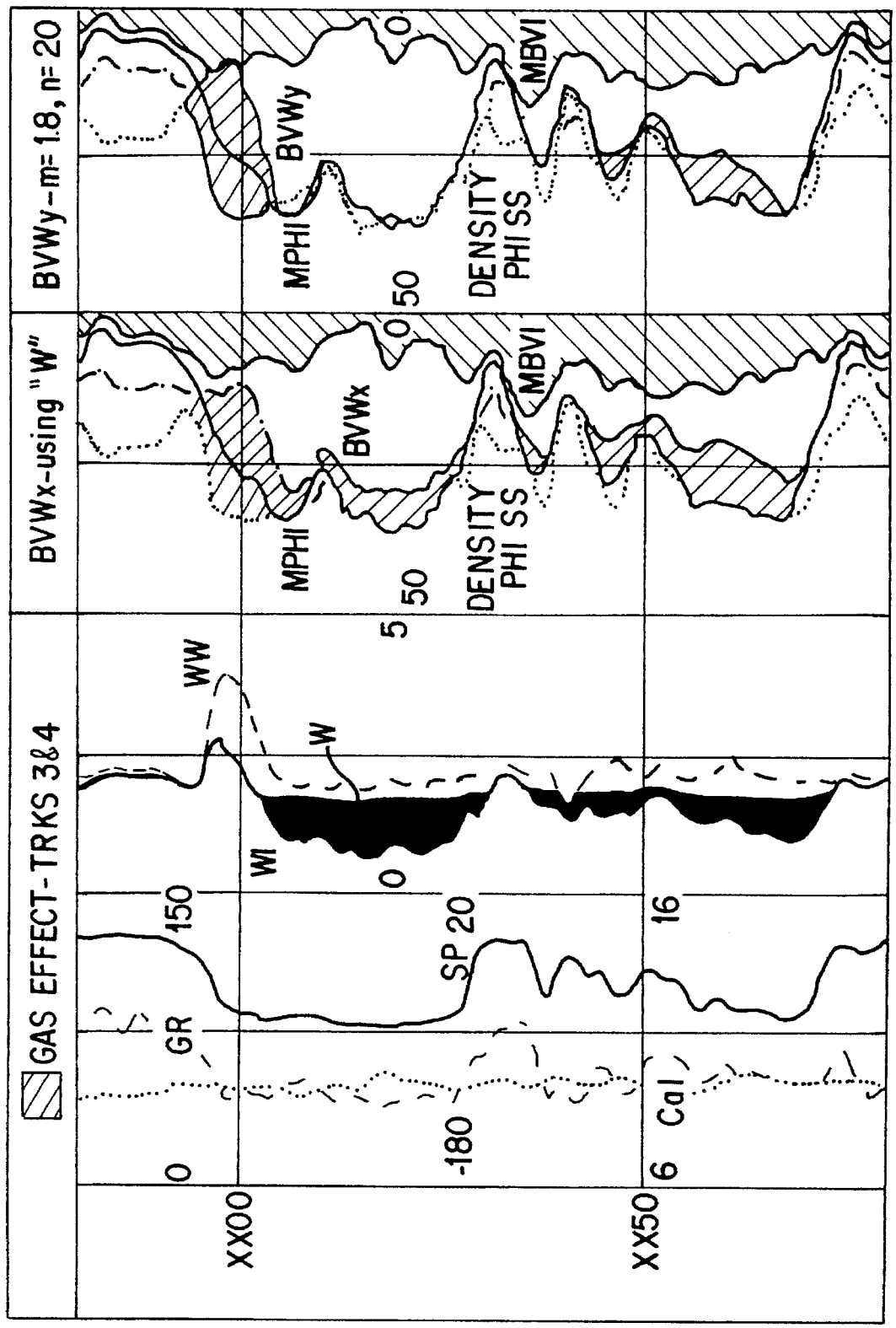
FIG. 8 is a comparison of conventional results (track 4) to those obtained by the method of the present invention (track 3) in determining bulk volume water for the formation of FIG. 3.

Track 2 of FIG. 8 shows a log of w (calculated using equation (4)), wi and ww for the above-described formation. The resulting bulk-volume water calculated using w, where the w to be used is constrained to be greater than or equal to wi and less than or equal to ww since ww and wi represent the endpoints of w, is shown in track 3 of FIG. 8. As can be observed, compared to the conventional "m" and "n" analysis depicted in track 4, the results have increased the water in some of the original "shows" while reducing it in others.

FIG. 8 also illustrates the capability of the w information to predict $S_{WIRR}$ qualities by comparing the predicted w to ww and wi. As can be observed, when ww>w hydrocarbons are present, and when w is greater than wi, a non-$S_{WIRR}$ zone is indicated. Only when w=wi, can the zone be considered at $S_{WIRR}$.

For the above-described formation, the show at the top of the upper sand of FIG. 8 was production tested, making 600 mcfpd of gas for 30 days then producing about 20 BWPD and 50 BOPD, finally leveling off at 100 BWPD and 40 BOPD.

EXAMPLE

Figure 9:
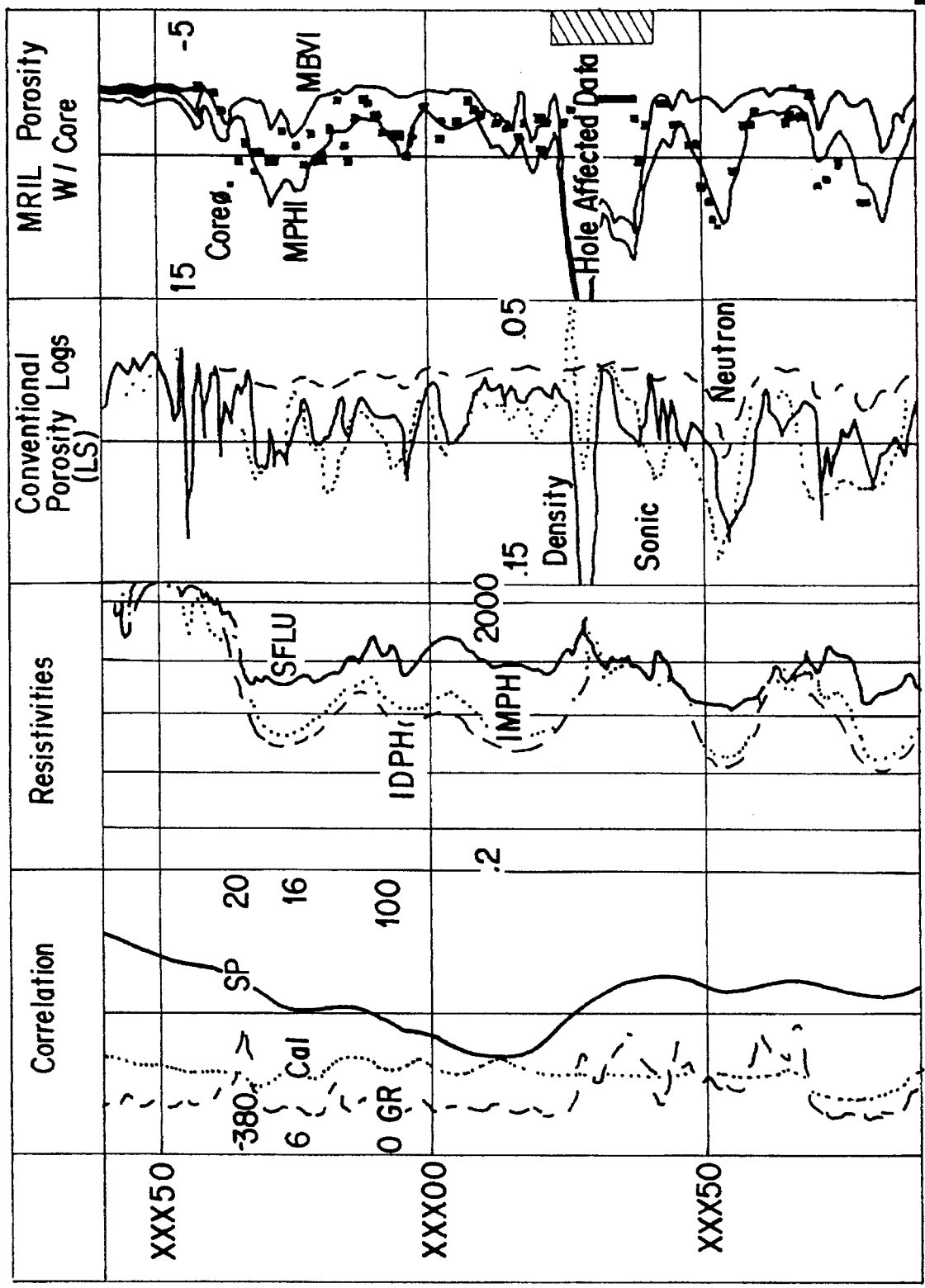
FIG. 9 is a log of a carbonate Edward's formation.

A carbonate formation more complex than the above-described shaly sand formation was investigated to verify the above-described results. FIG. 9 illustrates the log data for this formation. The interval shown is an Edward's formation from central Texas. As shown by the conventional porosity logs, (track 3 of FIG. 9) displayed in apparent limestone porosity units, the lithology is complex, and establishing the correct values for "a", "m", and "n" is difficult. However, the NMR derived porosity closely tracks the core derived porosity (track 4 of FIG. 9), demonstrating the NMR log's capability to determine porosity without concern for matrix lithology. Thus, the problem of determining porosity for a complex lithology is minimized, leaving the issue of relating porosity to formation factor.

Figure 10:
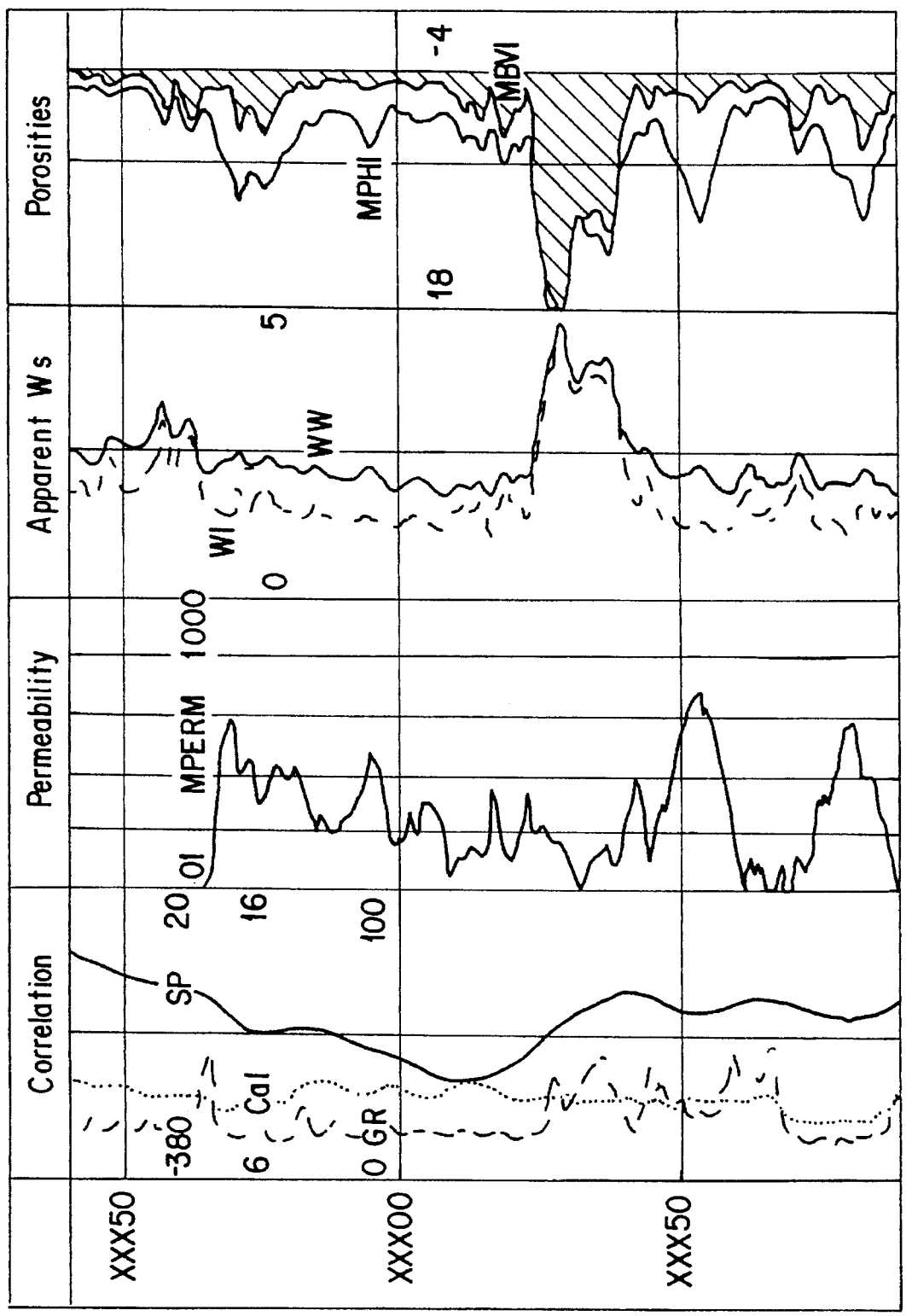
FIG. 10 is a comparison of the values of ww and wi for the formation of FIG. 9.
Figure 11:
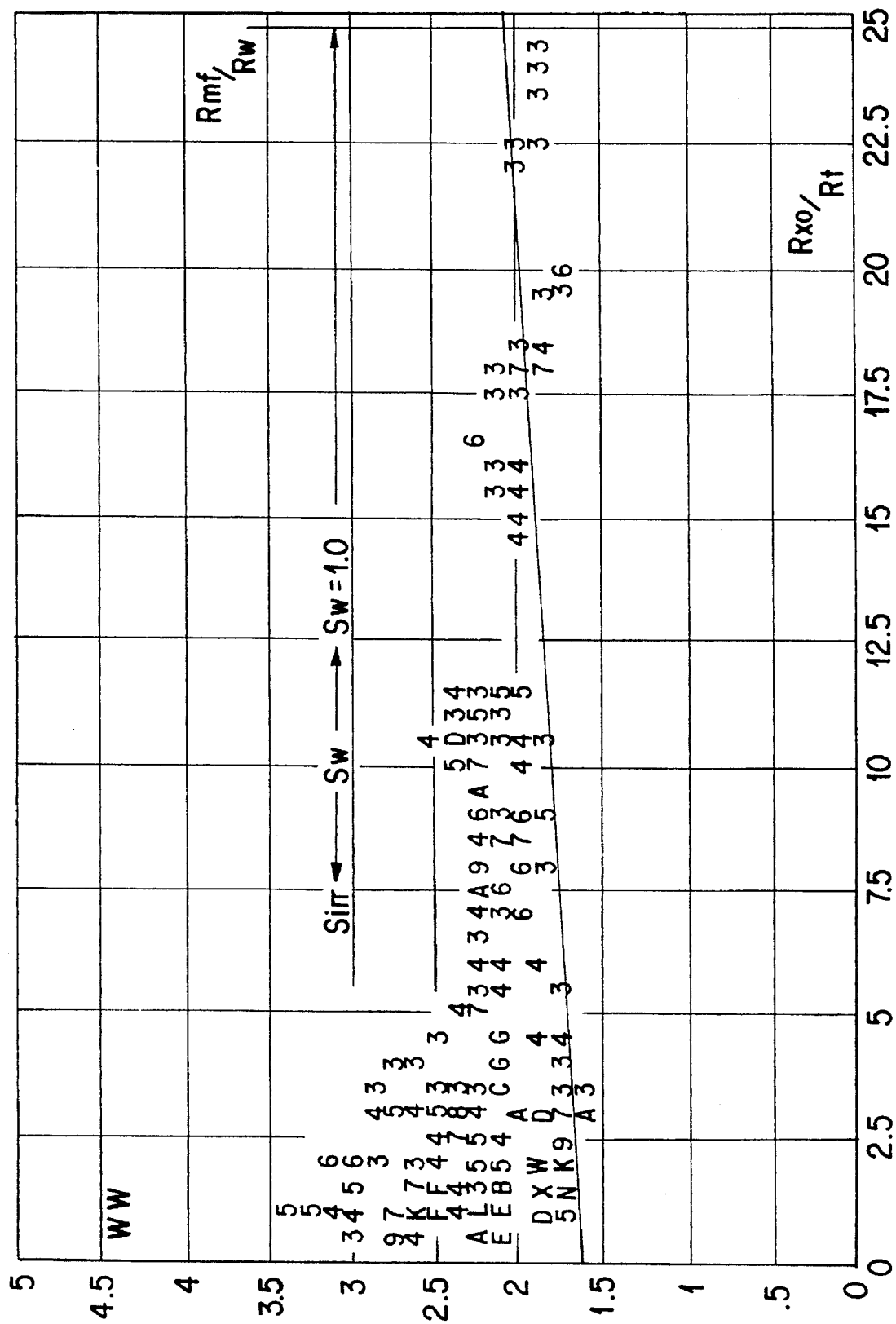
FIG. 11 is a comparison of ww and $R_{xo}/R_t$ for the formation of FIG. 9.
Figure 12:
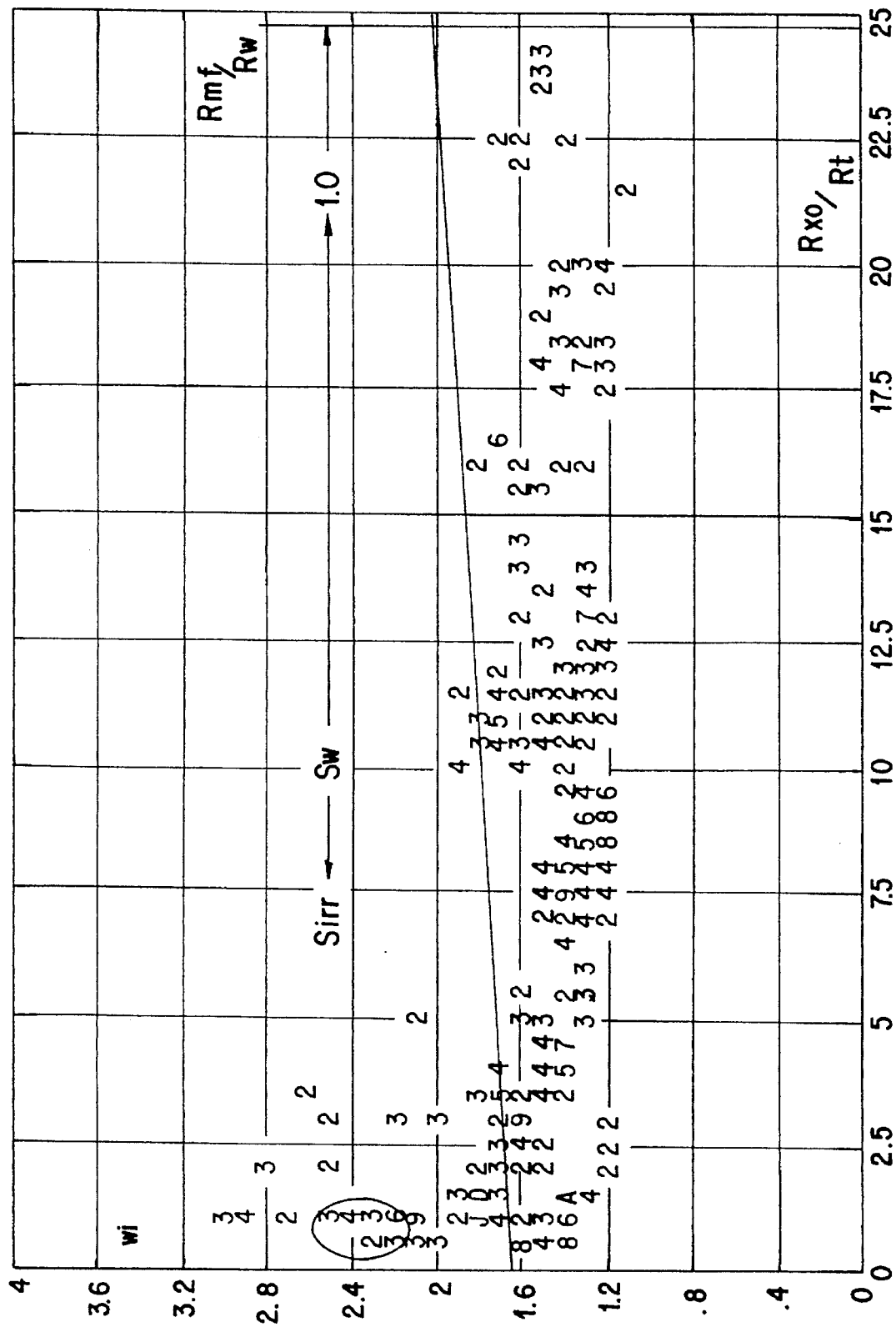
FIG. 12 is a comparison of wi and $R_{xo}/R_t$ for the formation of FIG. 9.
Figure 13:
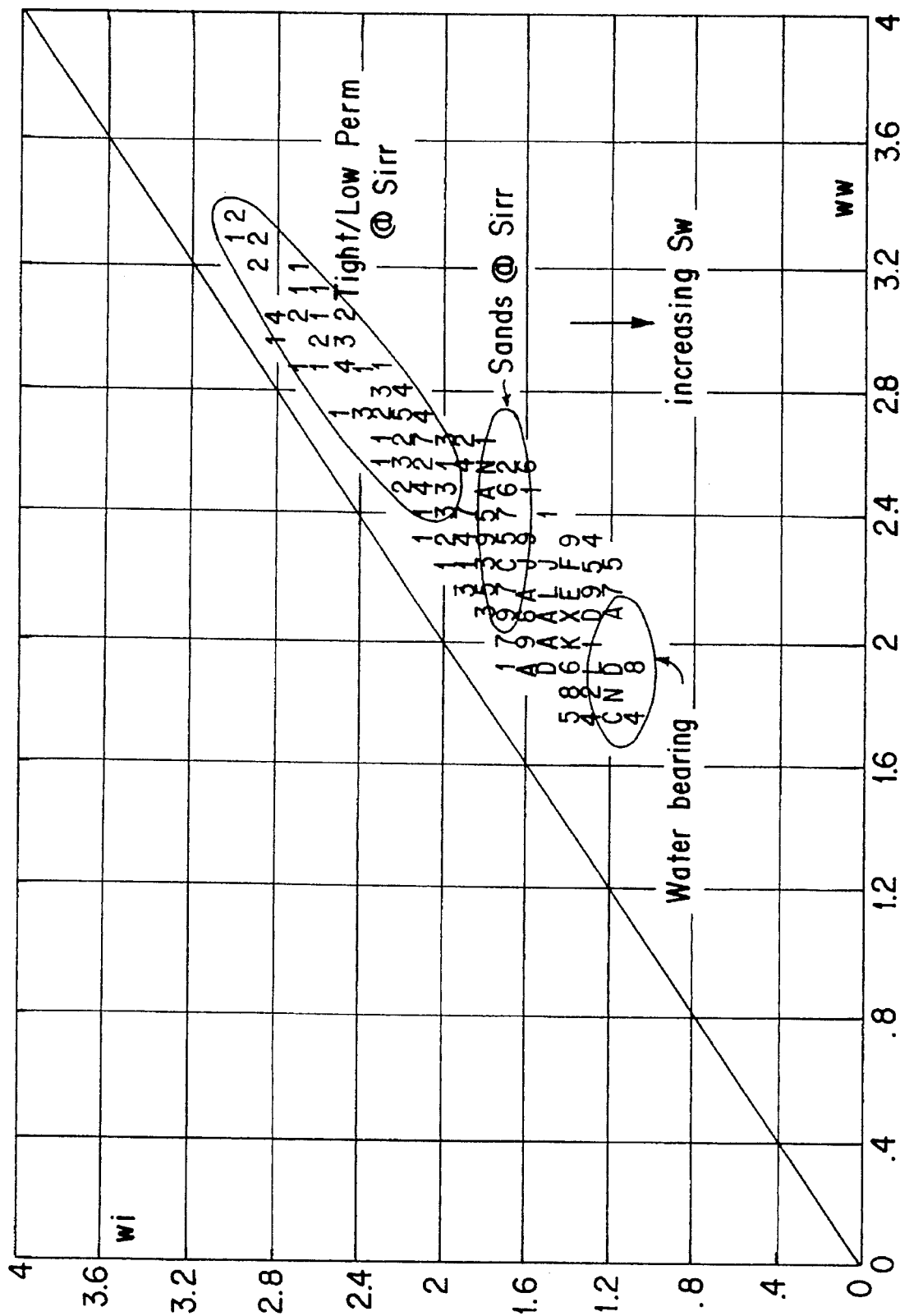
FIG. 13 is a comparison of wi and ww for the formation of FIG. 9.

The first pass analog results of wi and ww are shown in track 3 of FIG. 10. The ww versus $R_{xo}/R_t$ plot of this interval is shown in FIG. 11. The high $R_{xo}/R_t$ maximum gives good confirmation that a major portion of this interval has a high water content. Looking next at the BVI based wi versus $R_{xo}/R_t$ plot, FIG. 12, confirms the high water content and evidences that there are hydrocarbons present. This is indicated by the contrast in ww and wi in FIGS. 11 and 12. These conclusions are also supported by the trends observable in FIG. 13, a plot of wi against ww.

Figure 14:
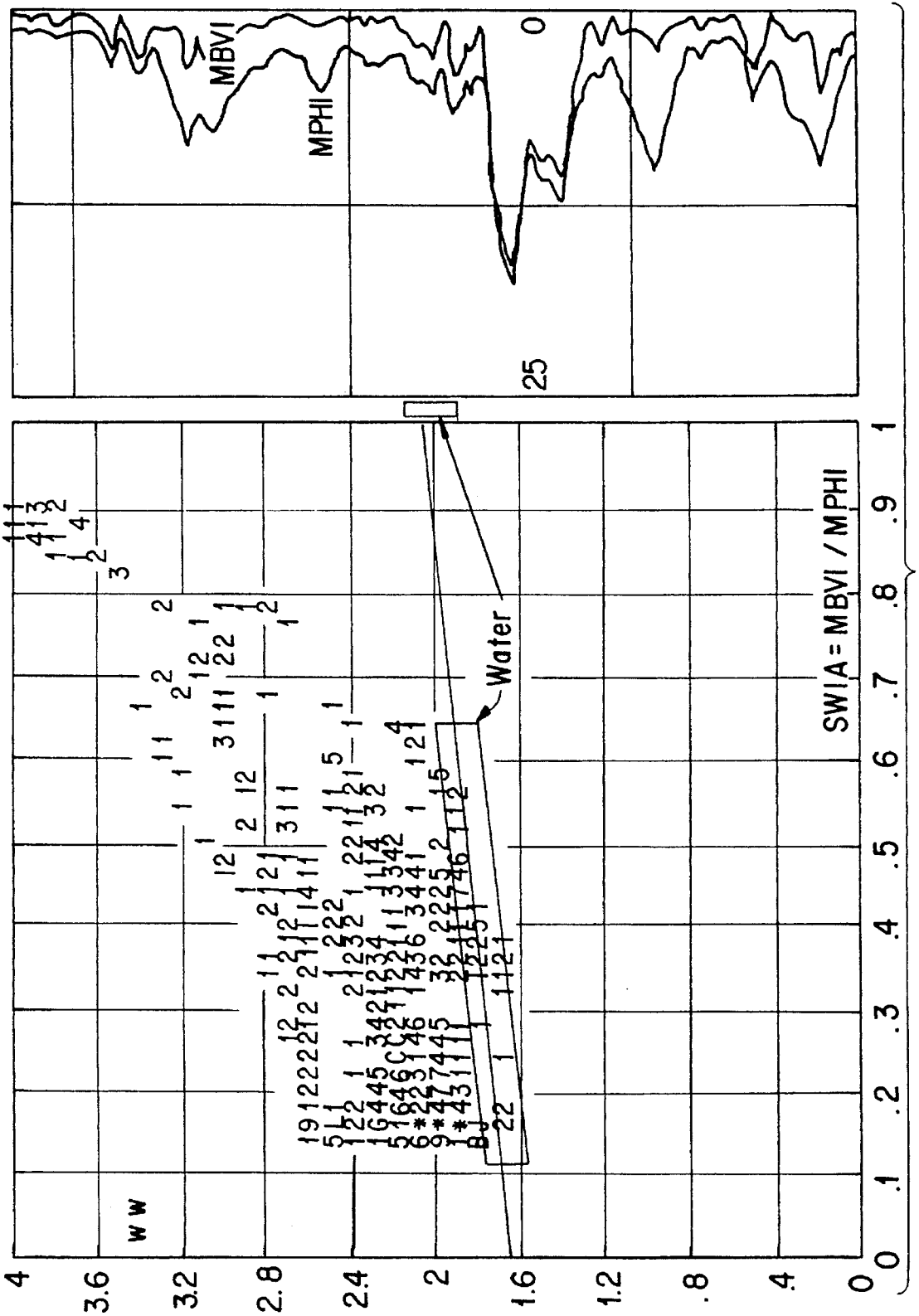
FIG. 14 is a comparison of ww and $S_{WIRR}$ (determined from the NMR measurements of bulk-volume irreducible water and porosity) for the formation of FIG. 9.

A comparison of ww to $S_{WIRR}$ is shown in FIG. 14, where $S_{WIRR}$ is derived from the NMR values of porosity and bulk volume irreducible as described above. The trend observed in the above-discussed Gulf-Coast shaly sand example in shown as a solid line (equivalent to Equation (4)). As can be observed, the solid line closely agrees with the lower edge of the data confirming the viability of Equation (4) to this type of formation. The data that falls above this line infers non-reservoir rock (shales) at $S_{WIRR}$ or hydrocarbon effects.

Table 1 shows the results of full core analysis on similar rocks from a nearby well in this field. The results of transforming the conventional a, m, and n values into w are also listed.

TABLE 1

| Depth | m | n | w | PHI | PERM | SAT |
|---|---|---|---|---|---|---|
| 10380.80 | 1.888 | 1.230 | 1.802 | 12.800 | 1.200 | 73.500 |
| 10382.60 | 2.063 | 1.020 | 1.738 | 6.300 | .510 | 28.600 |
| 10383.60 | 2.021 | 1.020 | 1.823 | 6.700 | .130 | 51.300 |
| 10451.40 | 2.119 | 1.120 | 1.796 | 9.200 | .910 | 32.00 |
| 10452.80 | 2.111 | 1.230 | 1.758 | 9.700 | 2.500 | 21.00 |
| 10453.40 | 2.055 | 1.160 | 1.688 | 11.200 | 5.500 | 21.900 |

Figure 15:
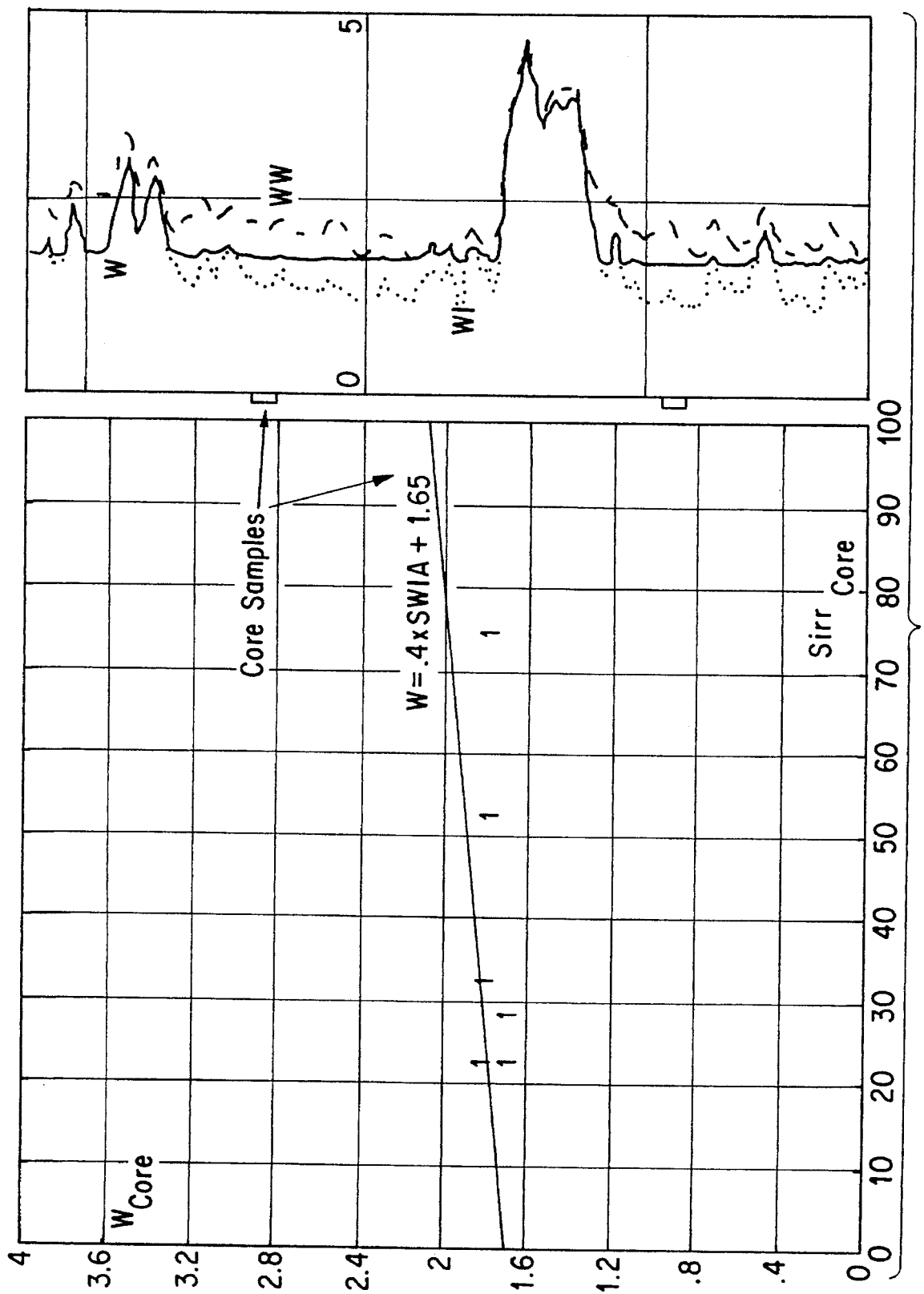
FIG. 15 is a comparison of core determined $S_{WIRR}$ and w for core samples taken from a well near the formation of FIG. 9.

FIG. 15 shows a plot of the derived w from Table 1 against core $S_{WIRR}$. Additionally, FIG. 15 also contains a solid line representing the trends observed on both the shaly sand and the log derived values shown in FIG. 14 (i.e., Equation 4). Though the data set is limited, it gives a fairly reasonable agreement to the observed trend.

Figure 16:
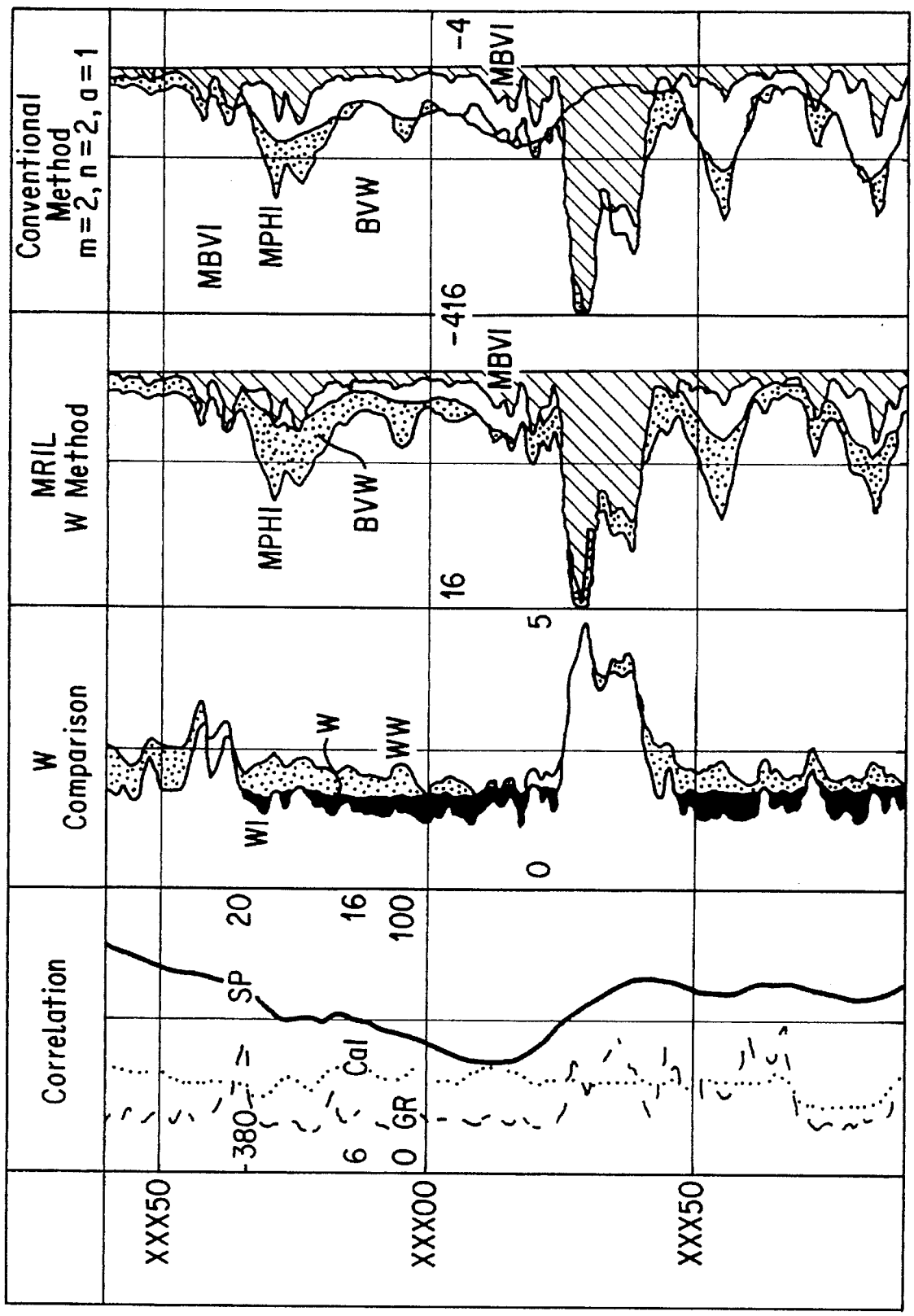
FIG. 16 is a comparison of convention results (track 4) to those obtained by the method of the present invention (track 3) in determining bulk-volume water for the formation of FIG. 9.

The actual w (as well as the apparent w's) calculated via equation (4) is shown in track 2 of FIG. 16. To determine the BVW term, the w to be used is first calculated via equation (4) and then constrained to be greater than or equal to wi and less than or equal to ww as discussed above. The results (track 3) show that most of the good permeability section is in a non-$S_{WIRR}$ state. The production tests on this well confirmed this by initially producing a 1.1 MMCF gas with low water flow from all major porosities in this interval. However, that quickly changed to non-commercial high water cut production in less than 60 days.

Using MRL Porosity Information

As briefly discussed above, observations of the porosity response of the magnetic resonance log (MRL) in comparison to other porosity measurements suggest a more direct method of determining the clay mineral water content of the formation than is generally available in conventional log data. In a paper by Coates et al., "The MRIL in Conoco 33-1: An investigation of a new magnetic imaging log," DD paper, 32-nd Annual Logging Symposium of the Society of Professional Well Log Analysts, Midland, Tex., 1991, the content of which is expressly incorporated by reference herein, it was observed that the MRL determined porosity is similar to the effective porosity used in conventional log interpretations because it does not take into account the contributions of pores of size less than about 2 μm. The reason is that such small pore sizes have very fast relaxation times which cannot be registered by the NMR tool. It is accordingly possible to model the MRL porosity measurement $PHI_M$ as being equal to the effective porosity, $PHI_{EF}$ using the following relationship:

$$PHI_M = PHI_{EF} = PHI_T - PHI_{CL}, \qquad (6)$$

where $PHI_T$ is the total porosity of the formation as measured by other independent methods, and $PHI_{CL}$ is the clay porosity of the formation. Dividing both sides of Eq. (6) by the total porosity $PHI_T$ and rearranging terms provides an expression for the free water saturation $S_{wf}$ and the bound water saturation $S_{wb}$:

$$S_{wf} + S_{wb} = 1. \qquad (7)$$

As well known in the art, total porosity $PHI_T$ estimates may be obtained from sonic logs, density logs or neutron logs, provided that the lithology of the formation is known. If the lithology is not known, or if mixtures of known minerals exist, a combination of two or more porosity and lithology sensitive logs can be used to define the lithology and provide an accurate value of the total porosity.

Figure 17:
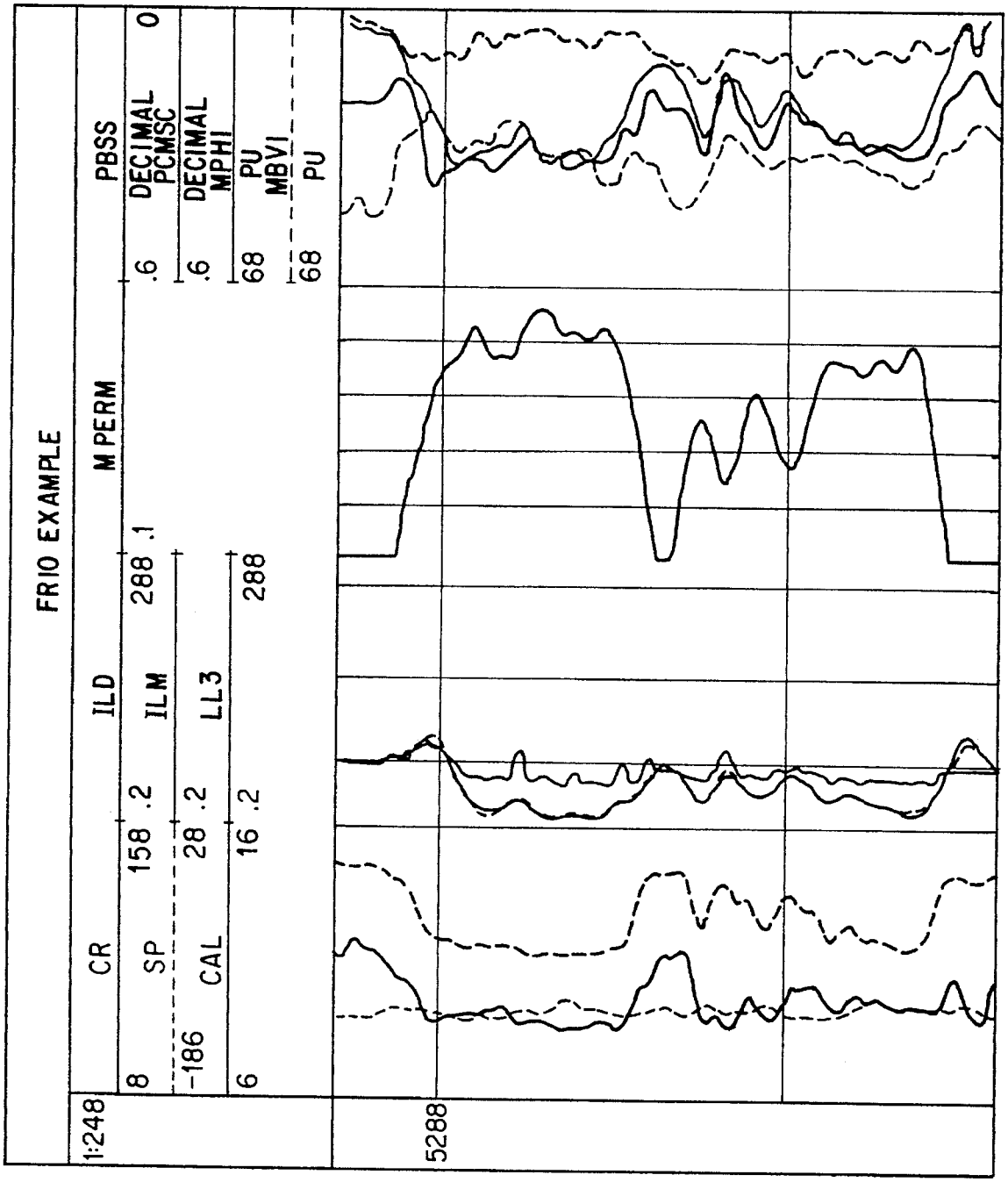
FIG. 17 is a comparison of the density-neutron MRL porosity measurements in a shaly sand.

Confirming the observation that the $PHI_M$ porosity measurement can be used to approximate the effective porosity $PHI_{EF}$ of the formation is the fact that in clastic, shaly sand conditions the MRL derived porosity $PHI_M$ is less than the total porosity $PHI_T$ measured by an independent method. On the other hand, in cleaner sands, such as those between 5212 ft and 5221 in FIG. 17 (track 4) the MRL porosity readings are close to the total porosity determined from a conventional density log.

Figure 18:
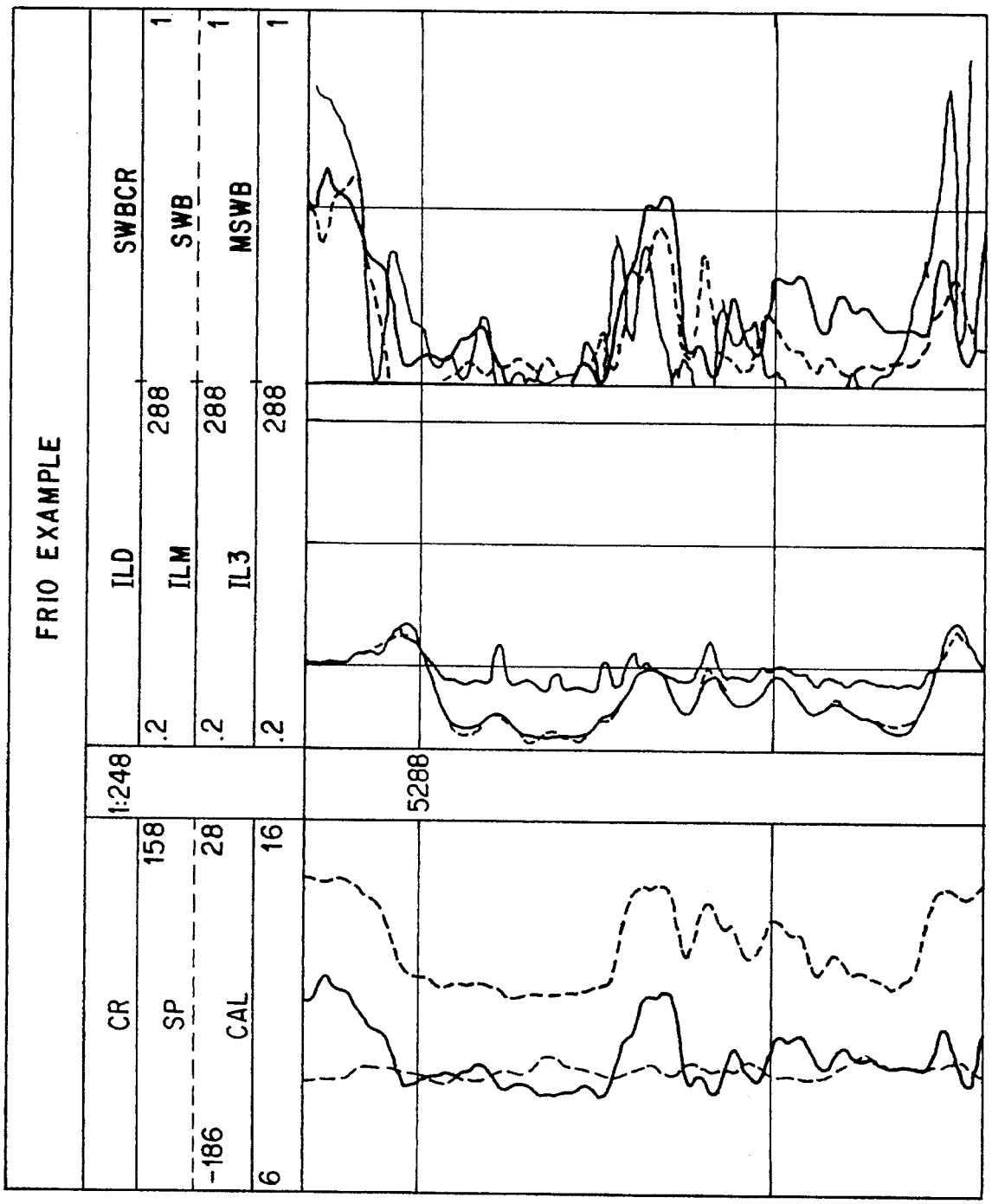
FIG. 18 is an illustration of clay bound water indicators correlation.

Track 3 in FIG. 18 illustrates the correlation between several clay bound water indicators including a gamma ray, a spontaneous potential and the MRL clay bound indicator in accordance with the present invention. It should be noticed that while the outputs of the indicators do not completely overlap, the output of the MRL indicator is clearly consistent with the other, more traditional indicators.

The comparison between MRL and density (or total) porosity measurements has been found sensitive to the inter-echo spacing (TE) used in the particular NMR experiment. Table 2 below indicates that the MRL porosity decreases as the spacing $T_E$ increases.

TABLE 2

MRL Core Analyzer Illustration of Porosity Sensitivity to Interecho Spacing.

| | | NMR CORE ANALYZER POROSITY | | |
|---|---|---|---|---|
| Sample | Core Porosity | TE = .5 ms | TE = 1 ms | TE = 2 ms |
| J7-A15-18 | 14.69 | 14.21 | 13.62 | |
| J7-B | 16.33 | 15.62 | 15.52 | 15.20 |
| J7-C | 14.17 | 14.04 | 13.56 | 13.18 |
| J7-D | 16.64 | 15.43 | 15.36 | 15.26 |
| J10-1 | 23.04 | 21.49 | 19.82 | 17.68 |
| J12-14 | 9.42 | 9.63 | — | 8.67 |
| J14-1 | 14.67 | 14.46 | 14.46 | 13.72 |

*Laboratory NMR measurements performed at static magnetic field gradient G = 6.74 gauss/cm The tendency of the $PHI_M$ measurement to decrease with an increase of the TE spacing, as illustrated in Table 2, indicates the existence of a relationship between the echo spacing of the NMR measurements and the porosity loss which is due to the presence of particular small pore-size components in the formation. Since small pore-sizes are related to the clay-mineral water content of the formation, in accordance with the present invention it is possible to directly estimate the clay porosity. Specifically, in a preferred embodiment of the present invention the value for the TE spacing is set equal to 2 msec, which value was found to be optimal for the determination of the clay porosity $PHI_{CL}$ of the formation. Smaller values for TE typically result in underestimating of the clay porosity, while larger values tend to eliminate porosity components which are of non-clay type, such as silt.

The derivation of the clay porosity $PHI_{CL}$ using the MRL measurements in accordance with the present invention in turn allows to determine the clay mineral bound water saturation $S_{wb}$ that can be used directly in the standard resistivity based models to obtain accurate water saturation estimates, as well as other parameters of interest, such as the effective bulk volume water and the permeability of the formation.

Specifically, turning back to Eq. (1), the Archie formation factor analysis formulas can be rewritten to assume the form:

$$(PHI^m S_w^n) C'_w = C_t \qquad (8)$$

where C' is a general conductivity term corresponding to a clean formation. For shaly formations the C' conductivity can be expressed as a function of the free water conductivity $C_W$, the water bound saturation $S_{wb}$ and a clay water conductivity parameter $C_{cw}$ which can be obtained using the Dual-Water CEC method, as discussed for example in Clavier et al., "The Theoretical and Experimental Bases for the 'Dual Water' Model for the Interpretation of Shaly Sands," SPE 6859, Annual Technical Conference and Exhibition of the Society of Petroleum Engineers Journal, Denver, Colo., October, 1977. As discussed in this paper, the clay water conductivity $C_{cw}$ is a function of the formation temperature Tf and is given by the expression:

$$C_{cw} = 0.000216 * (Tf + 504.4) * (Tf - 16.7) \qquad (8A)$$

Assuming a single exponential w model, as discussed above, and using the water conductivity expression for shaly formations, Eq. (8) can be rewritten as follows:

$$BVW^w[C_W(1 - S_{wb}/S_{wt}) + C_{cw} S_{wb}/S_{wt}] = C_t \qquad (9)$$

where $S_{wt}$ is the total water saturation. The expression in Eq. (9) is equivalent to the one in Eq. (2), so once again it is possible to determine values for the apparent wi and ww exponential factors. In Eq. (9) however, all quantities can be determined directly from the MRL log measurements.

In particular, if the total water saturation is assumed to be $S_{wt} = 100\%$, the value of the full-water ww exponential parameter can be obtained from Eq. (9) by noticing that $BVW = PHI_T$, and $S_{wt} = 1$. All other quantities are directly determinable from the MRL measurement so that the ww parameter can be computed as:

$$ww = \log_{10}[C_t/(C_w + S_{wb}*(C_{cw} C_w)]/\log_{10}(PHI_T); \qquad (10)$$

Conversely, if the total water saturation $S_{wt}$ is assumed to be at irreducible level, $BVW = BVI_T$, as defined above. The total bulk volume irreducible water $BVI_T$ can be expressed as follows:

$$BVI_T = PHI_T * (S_{irrcl} + S_{irrncl})$$

where $S_{irrcl}$ is the irreducible saturation component due to clay minerals and $S_{irrncl}$ is an irreducible saturation component due to non-clay factors. The $S_{irrncl}$ factor may be computed directly from a measurement of the MRL bound volume irreducible $BVI_M$ and is equal to:

$$S_{irrncl} = BVI_M/PHI_T.$$

Substituting and simplifying the expression gives the following formula for the wi exponential parameter:

$$wi = \log_{10}[C_t/(C_w + S_{wbi}*(C_{cw} - C_w)]/\log_{10}(BVI_T) \qquad (11)$$

where $S_{wbi}$ is the irreducible bound water saturation.

The effective exponential parameter w given in Eq. (5) may now be directly computed from the MRL measurements in accordance with the present invention and is given by the expression:

$$w = 0.4 * BVI_M/PHI_M + 1.65 \qquad (12)$$

The solutions in Eq. (10), Eq. (11) and Eq. (12) present a substantial advance over the prior art because they allow the log analyst to avoid the use of the current very subjective approaches to determining the Swb parameter.

Corrections for Additional Factors

In the application of the method of the present invention to MRL measurements, it is important to recognize that other factors may influence the accuracy of the proposed model. Two specific cases are easy to recognize: the presence of gas in the measurement pore space; and the presence of micropores associated with ferromagnetic or paramagnetic materials. For example, it has been observed that in a gradient magnetic field of the type used in the above described logging tools the porosity measurements are sensitive to the diffusion coefficient D. Accordingly, if some of the pore space of the formation is gas filled, the tool will not register it.

Both cases considered above may result in situations where the MRL tool of the present invention may underestimate the actual formation porosity and as a result overestimate the clay bound water content. Two possible approaches are possible in order to correct this effects. The first approach is to utilize several clay bound water indicators which are less sensitive to the presence of gas or ferromagnetic materials. The second approach utilizes an iterative process constraining the values of the computed clay porosity parameter.

In accordance with the present invention, when using the second correction approach the criterion for applying a correction is expressed as the following condition:

$$BVW_T(res) \geq BVI_T(M)$$

where $BVW_T(res)$ is the total bulk volume water as determined from a resistivity measurement and $BVI_T(M)$ is the total bulk volume irreducible water, as determined by the MRL tool. This condition recognizes the fact that the total water volume found in the formation cannot be less than the total bound water volume. If the condition is satisfied, the method of the present invention makes no corrections to the computed values.

If the condition is not satisfied, three possible corrections may be considered, dependent on the values of the apparent water conductivity $C_{WA}$ and the clay water conductivity $C_{cw}$, as defined above.

If $C_{WA}=C_{cw}$, in accordance with the method of the present invention, an error flag is posted indicating to the log analyst that an independent external correction must be made in the value of the $R_W$ parameter in the Archie factor analysis.

If $C_{WA}>C_{cw}$, an error flag is posted indicating that an independent correction must be made in the value of the apparent water conductivity. Finally, if $C_{WA}<C_{cw}$, it is assumed that the error is in the computed value of the $S_{wb}$ parameter, in which case an iterative correction to the computed value of the clay bound water volume is initiated.

Figure 19A:
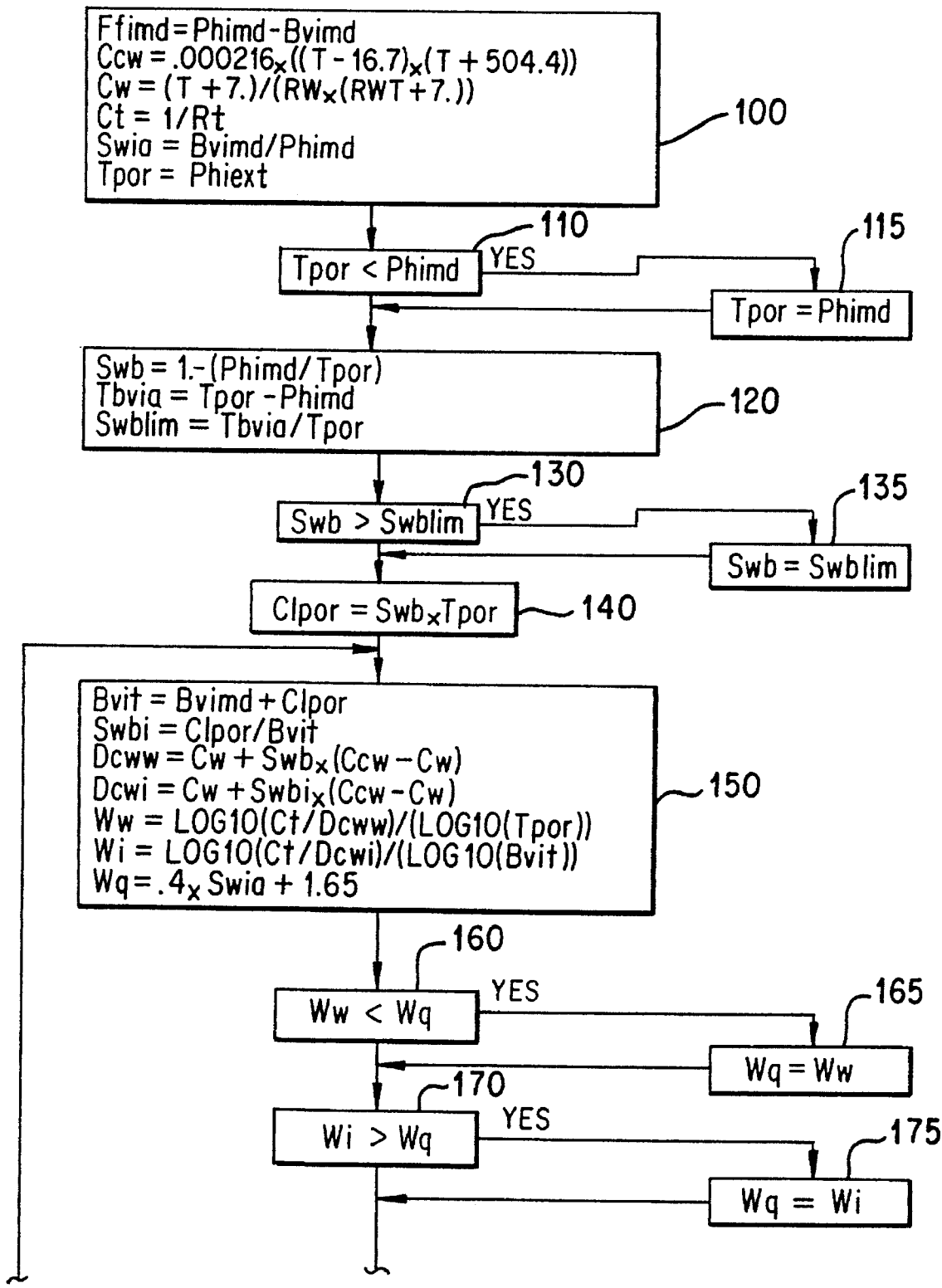
FIG. 19 is a block diagram of the MRL analysis method in accordance with the present invention.
Figure 19B:
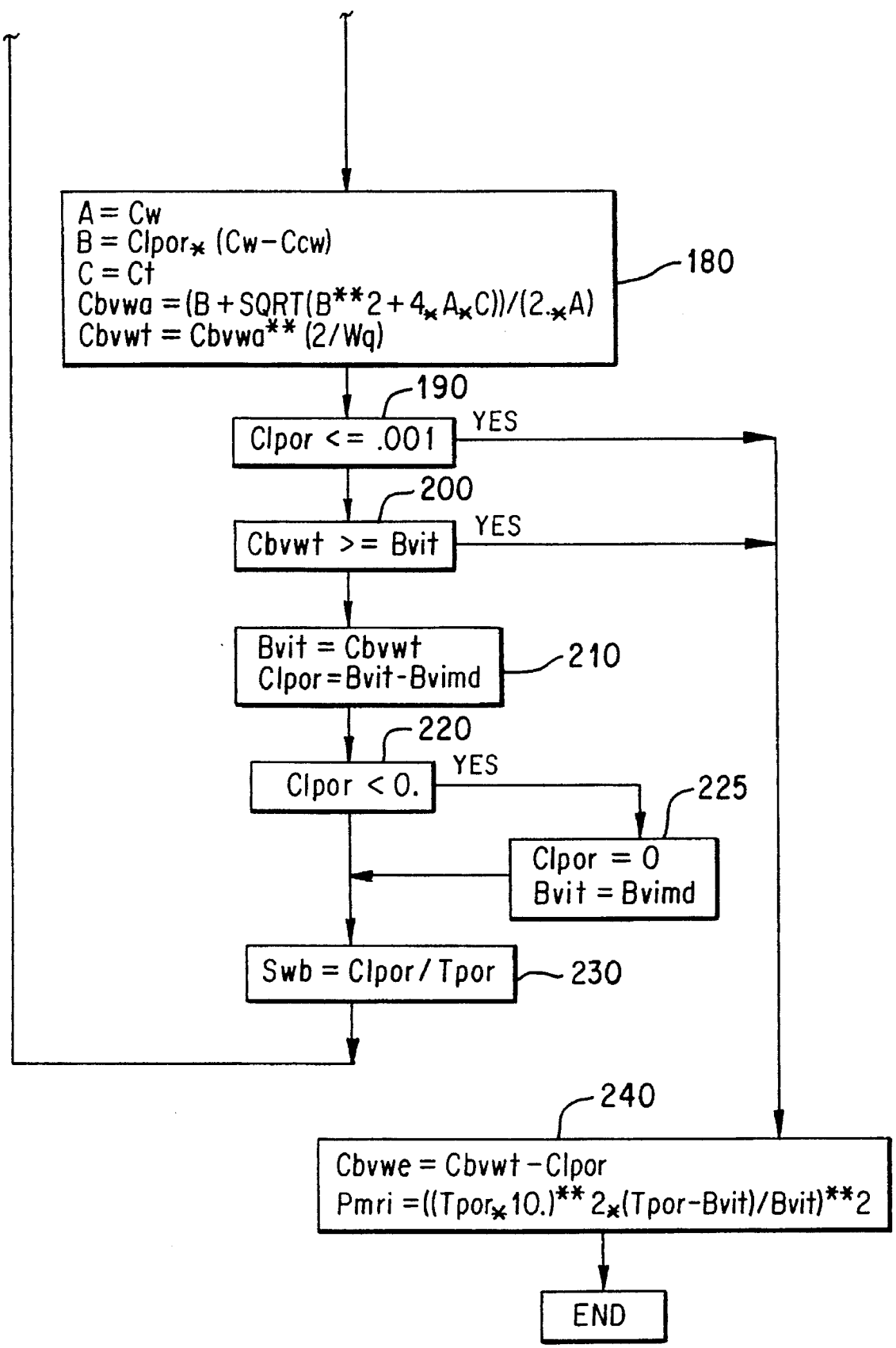

FIG. 19 illustrates in a block diagram form the MRL analysis method in accordance with the present invention which corresponds to the third correction, as discussed above, and provides the capability to compensate for additional factors which influence the accuracy of the MRL measurements.

In step 100 the values of several internal parameters are computed and stored in a computer memory. These internal parameters include the total porosity of the formation as determined by independent measurements and the values for the MRL determined free fluid index, the clay and the free water conductivities, and the temperature T and conductivity $C_t$ of the formation.

In steps 110 the algorithm checks whether the total porosity value is less than the porosity $PHI_M$ determined from the MRL measurement, and if this conditions met, in step 115 assigns the value of the total porosity equal to the MRL measured porosity value.

In step 120 are computed the bound water saturation $S_{wb}$, the apparent total bulk volume irreducible water and the bound water saturation limit in accordance with the present invention. In steps 130 and 135 the computed bound water saturation $S_{wb}$ parameter value is checked versus its limit value defined in step 120, and is set equal to $S_{wblim}$ if it is greater. In the following step 140 the clay porosity is computed from the values of the total porosity and the bound water saturation.

In step 150, the values of several output parameters are computed in accordance with the expressions in Eqs. (10–12). In steps 160 to 175 the methods checks whether the variable w exponential value falls within the range of values defined by the boundary values wi and ww, and if outside this range in either direction, assigns a value for w equal to the corresponding boundary value.

In step 180 are computed the values for the apparent ($BVW_A$) and total ($BVW_T$) conventional bulk volume water parameters. Method steps 100–180 comprise the MRL analysis where no corrections are made. In step 190, if the computed clay porosity $PHI_{CL}$ value is smaller than certain threshold, set in a specific embodiment of the present invention equal to 0.001, control is transferred to step 240, in which the effective $BVW_{EF}$ is computed. In step 240 the permeability PERM of the formation may also be computed in accordance with the formula:

$$PERM_M = 100*(PHI_T)^2*[(PHI_T-BVI_T)/BVI_T]^2.$$

Method step 200 initiates the correction, as described above by checking whether the bulk volume water $BVW_T$ is greater than the bulk volume irreducible water $BVI_T$. If the condition is satisfied, the method transfers control to step 240. If the condition is not satisfied, in step 210 $BVW_T$ is set equal to the $BVI_T$ parameter, and the clay porosity $PHI_{CL}$ is set equal to $PHI_{CL}=BVI_T-BVI_M$.

In steps 220 and 225 if the clay porosity $PHI_{CL}$ computed in step 210 is negative, its value is set equal to 0, and the $BVI_T$ parameter is set equal to the MRL-computed $BVI_M$ value. Finally, in step 230 the bound water saturation parameter $S_{wb}$ is set equal to the corrected clay porosity $PHI_{CL}$ divided by the total porosity $PHI_T$ and the method returns back to step 150. The iteration is continued until the condition in step 210 is satisfied. Appendix A presents a definition of all parameters used in the analysis in FIG. 19 which in some cases deviate from the notations used in the description above.

Figure 20:
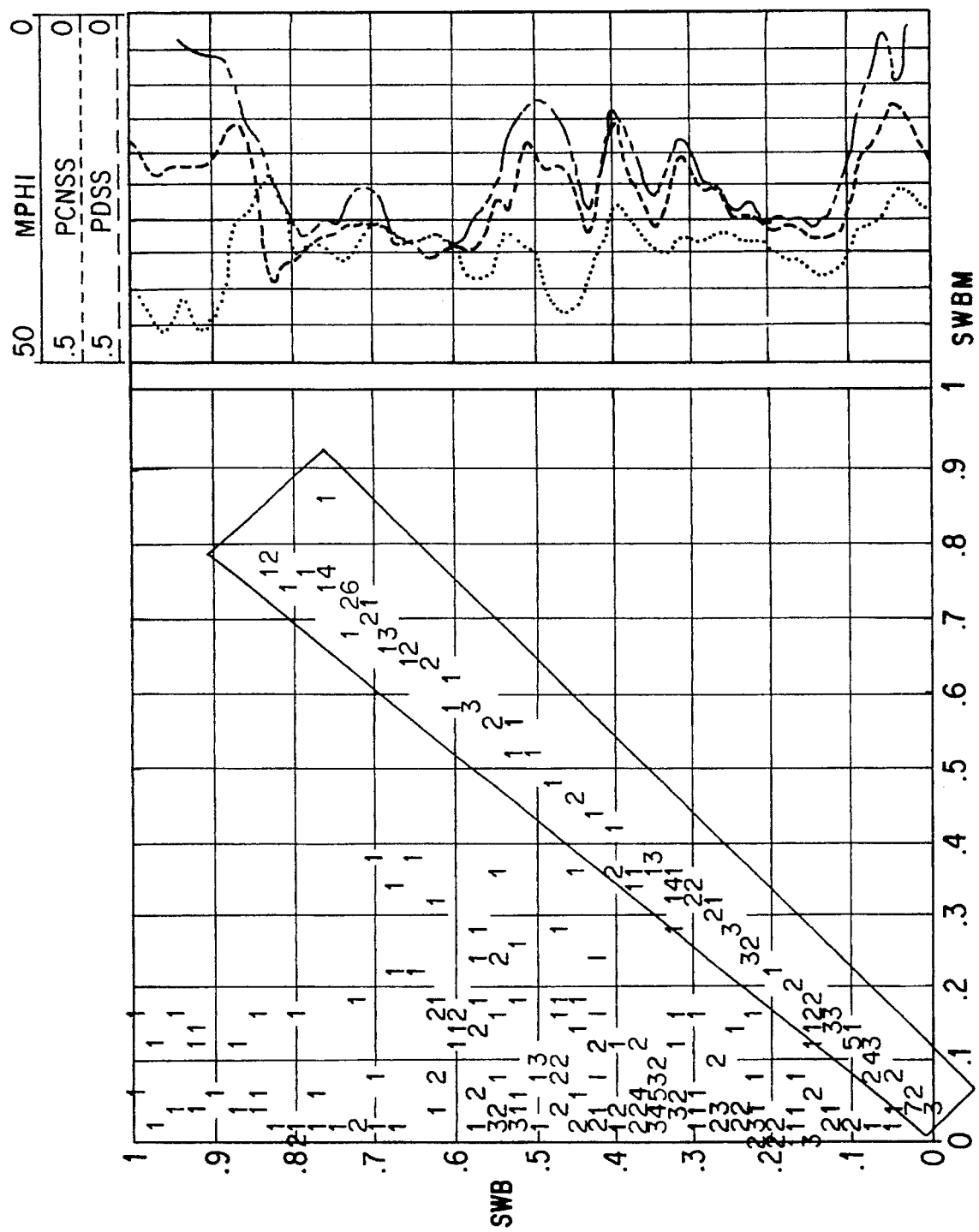
FIG. 20 is an illustration of a comparison of $S_{wb}$ obtained from $C_{wa}$ and the MRL method of the present invention.

FIG. 20 illustrates a comparison of the values for the water bound saturation $S_{wb}$ computed using a conventional resistivity log method and the MRL method in accordance with the present invention. The plot clearly illustrates a good agreement of the computed parameters in both cases.

Figure 21:
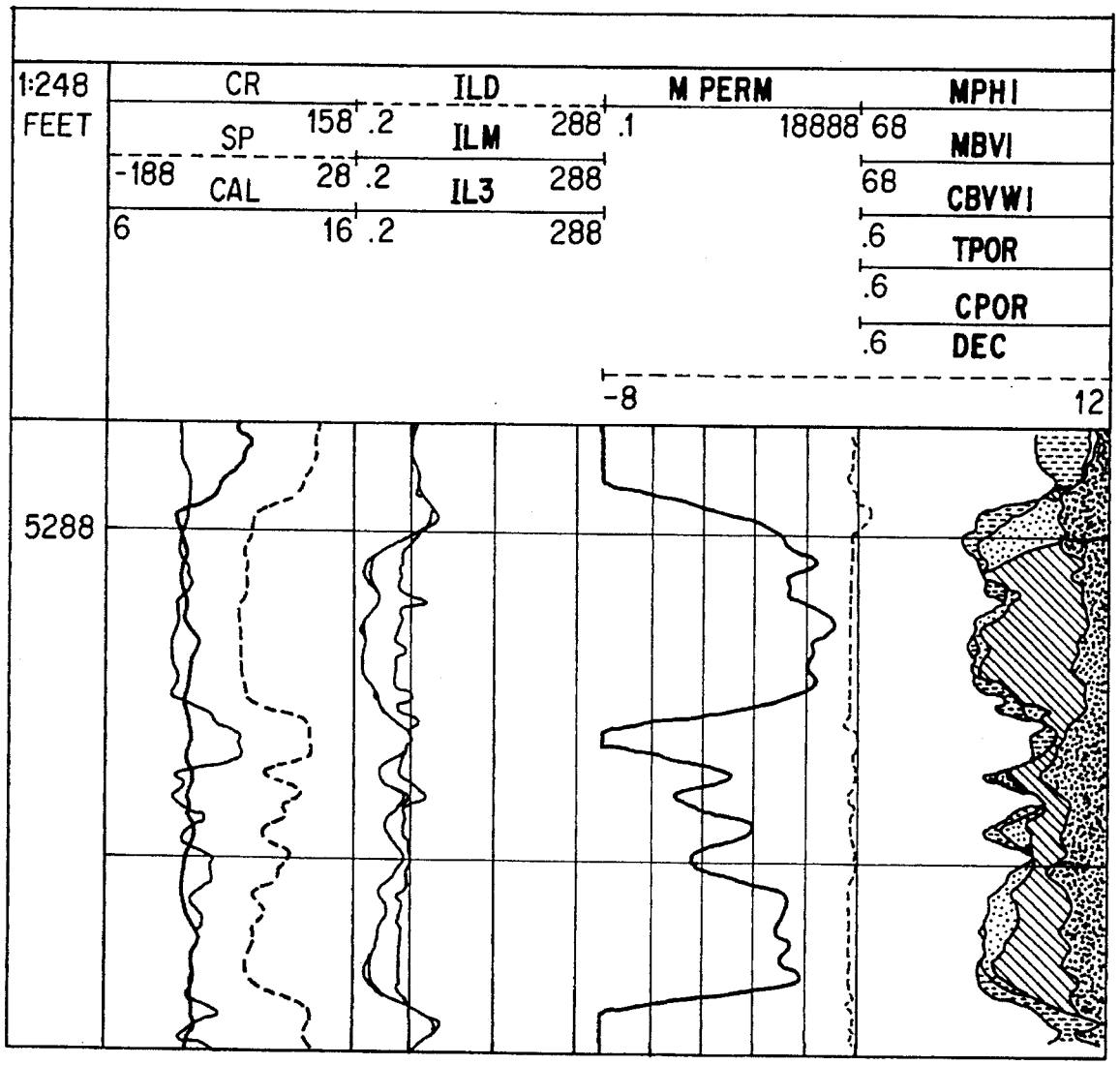
FIG. 21 illustrates the results obtained from the method of the present invention in the computation of $S_{wb}$ in a Frio Shaly sand example.
Figure 22:
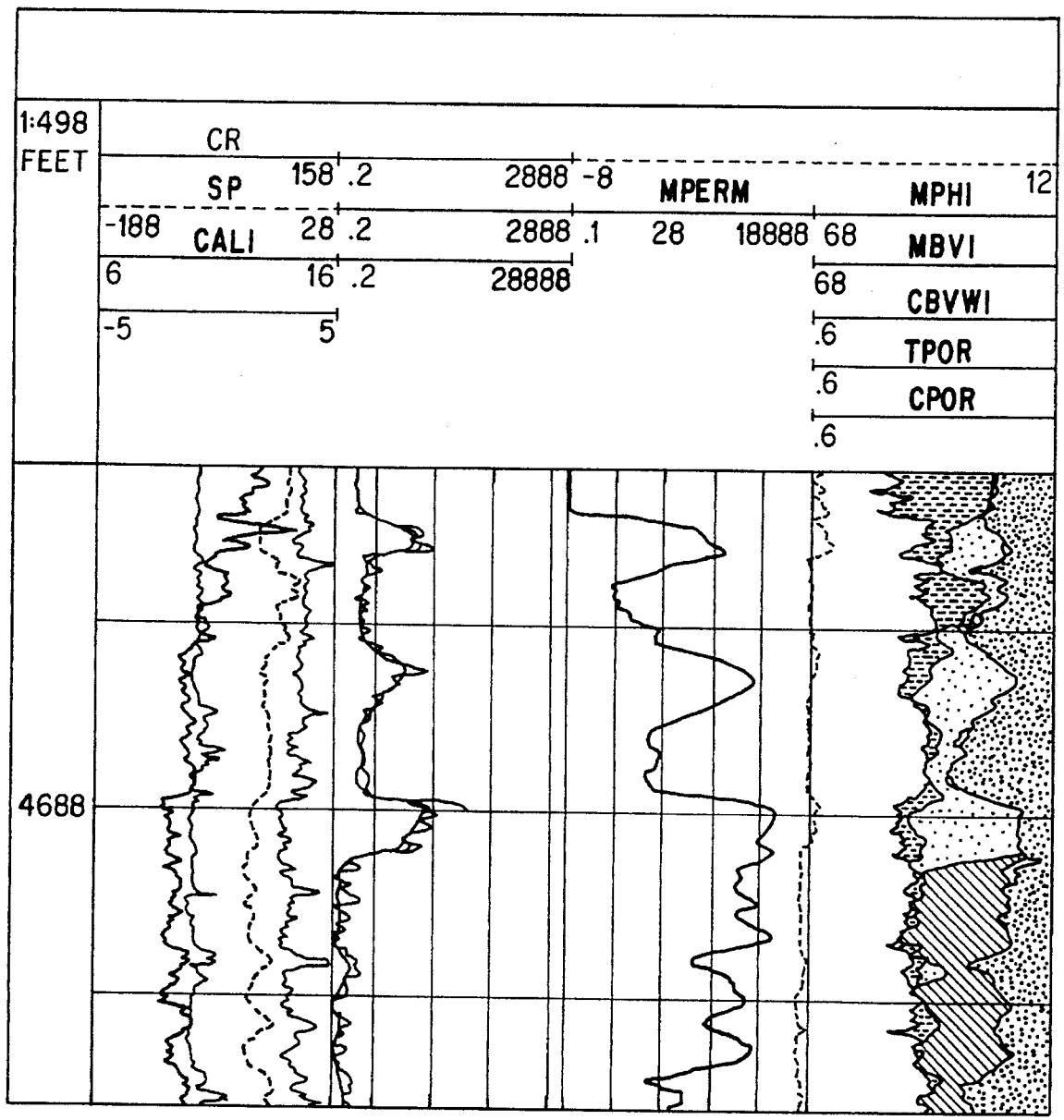
FIG. 22 illustrates the results obtained from the method of the present invention to the computation of $S_{wb}$ in a Gulf of Mexico Eugene Island example.

Tracks 4 in FIGS. 21 and 22 illustrate the potential of the method of the present invention to detect the presence of clay, and free fluid space including hydrocarbons and producible water.

The following paragraphs provide additional information as well as alternate description of the present invention which may be useful in clarifying certain aspects of the inventive concept.

Though the data displayed in track 3 of FIG. 18 demonstrates a good correlation between this clay indicator and conventional indicators, it does not demonstrate an absolute tie to a quantitative value. This in fact reflects the limitation of other conventional approaches as well since they are subject to an analyst's parameter selection.

Thus, it is necessary to demonstrate that the result from Eq. (6) provides a quantified measure of clay bound water. It is possible to do this through use of a CEC model by using conventional porosity and resistivity log data, i.e., when the total water saturation Swt=1, the true formation conductivity Ct is given by:

$$Ct=(PHI^m{}_T)*(Cwf+Swb(Ccw-Cwf)) \qquad (13)$$

where m is the cementation exponent, and Cwf and Ccw—are the free and bound water conductivities, respectively. The clay bound water saturation Swb is related to CEC per unit pore volume (Qv) according to Swb=$\alpha V_Q Q_v$, where V is the volume of clay-bound water per unit charge on the clay and $\alpha$ is a factor that depends on salinity. (See Clavier et al., "The Theoretical and Experimental Bases for the 'Dual Water" Model for the Interpretaiton of Shaly Sands," paper SPE 6859, presented at the Annual Technical Conference and Exhibition of the Society of Petroleum Engineers Journal, Denver, Colo., October 1977.)

Figure 23:
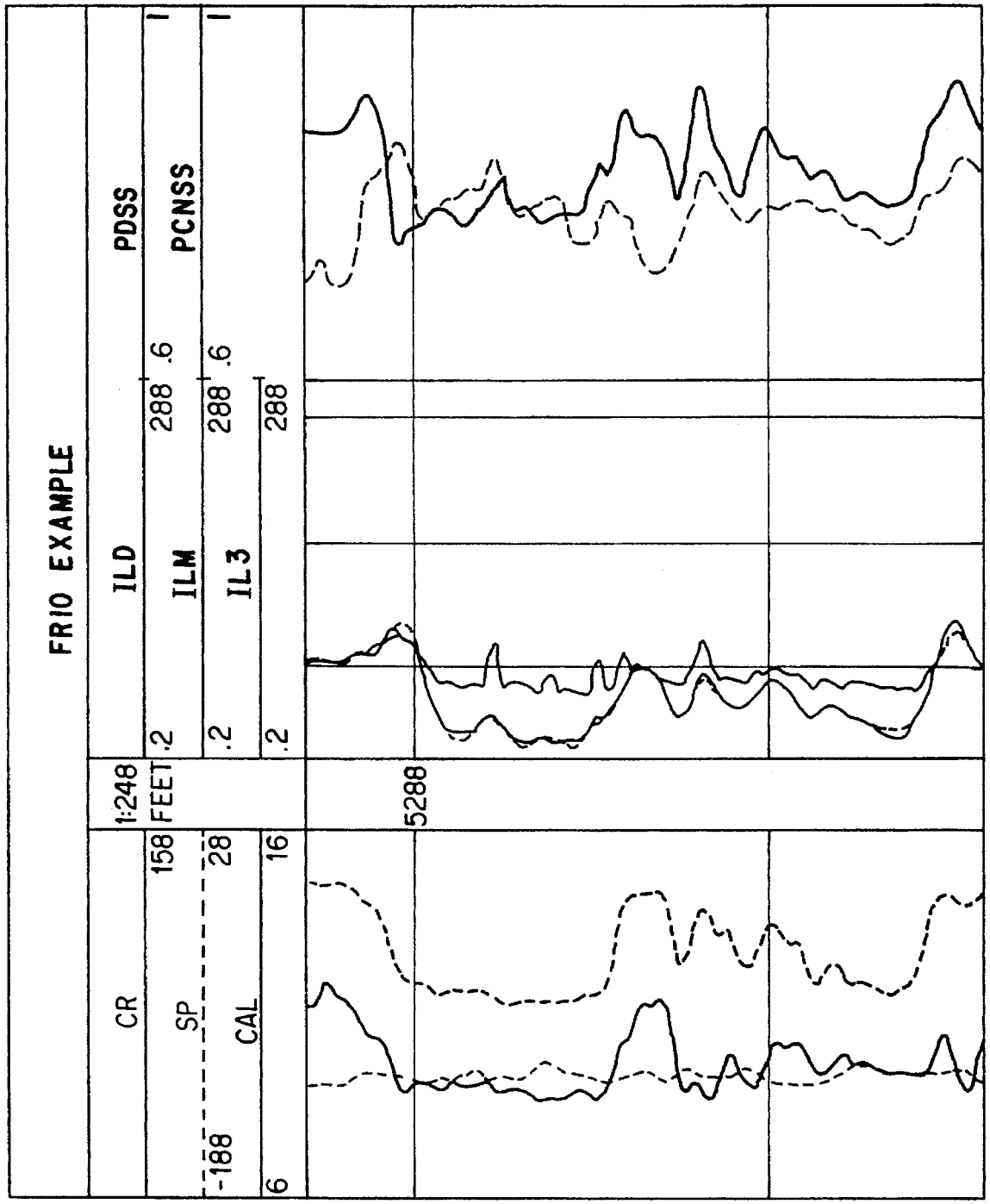
FIG. 23 illustrates a water bearing Frio shaly sand interval from the Texas Gulf Cost.

By definition, the CEC influence on a resistivity log is determined by the change in apparent water resistivity as seen in water bearing shaly sands. (Clavier et al., 1977). This is demonstrated from solution of Eq. (13) using the expressions for theoretical clay water conductivity, the free water conductivity, and a measure of Rt. The triple-combo log shown in FIG. 23, across a Frio sand from the Texas coastal area, illustrates a shaly sand that is appropriate for this purpose.

The apparent porosity derived from neutron-density crossplots is often used as a measure of total porosity. This often gives reasonable results in the reservoir sandstones but tends to over-call the porosity as a function of clay content.

This can create a dilemma when efforts are made to use any theoretical CEC model since it is necessary that the measured resistivity balance with clay content in the formation water conductivities using the expression for the formation factor F in Eq. (1).

These issues are readily seen in the following Eq. (14) which shows the Archie relationship used to transform resistivity into apparent water resistivity, and in Eq. (15) where the apparently bound water fraction is related to the apparent water conductivity and the end point values for all clay bound water or all non-clay water, i.e.;

$$Rwa = Rt/F; \quad (14)$$

$$Swb = (Cwa - Cwf)/(Ccw - Cwf). \quad (15)$$

As Eq. (14) shows, the resulting Rwa is dependent on the porosity (Phit) as well as the exponent m. In many shaly sand studies it has been shown that sandstones typically have m≈1.8 and a≈1. In shales these parameters are not well known, although some laboratory data suggests m increases with clay content.

Figure 24A:
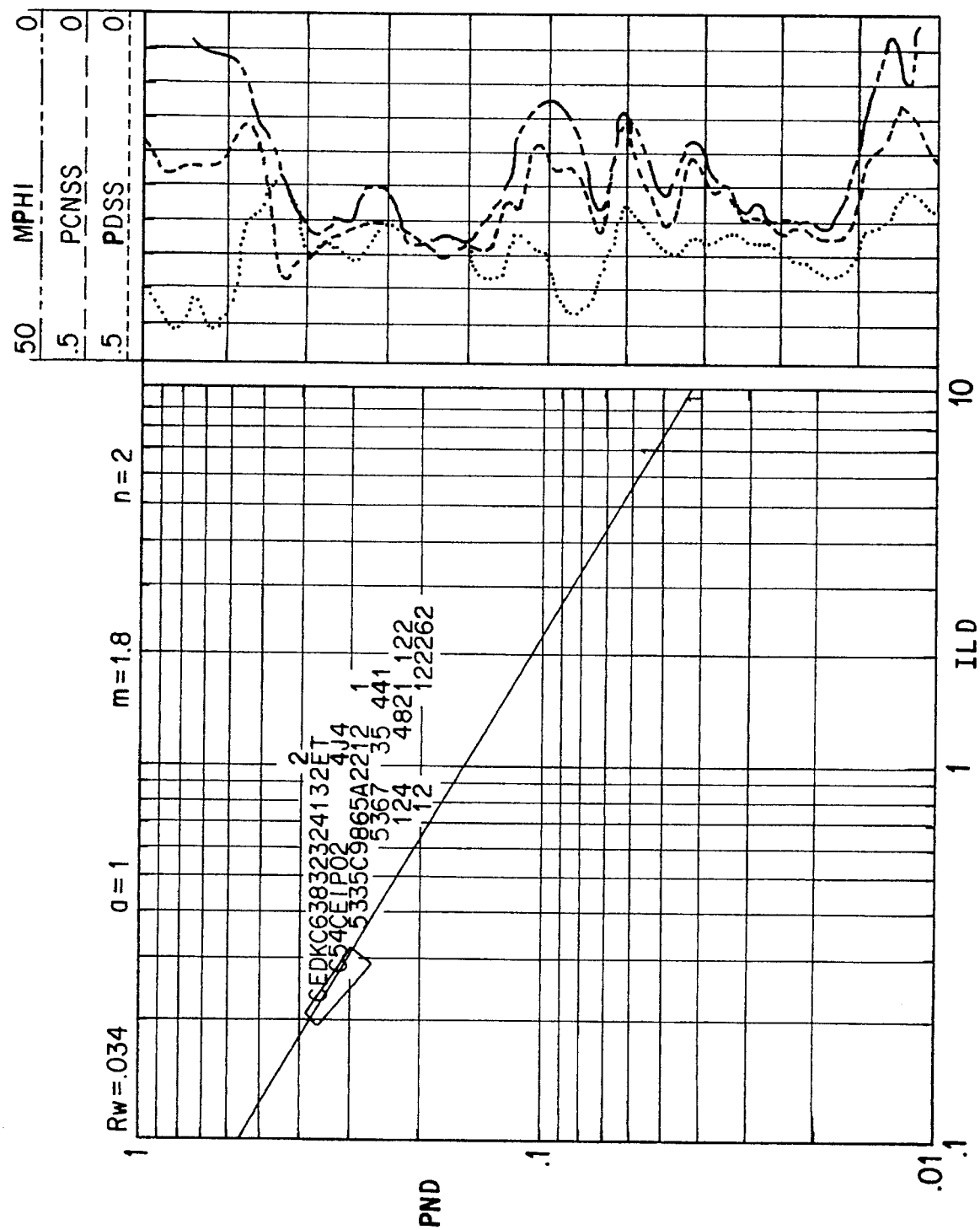
FIG. 24 A is a Pickett plot illustrating Rw using Density-Neutron Crossplot porosity.
Figure 24B:
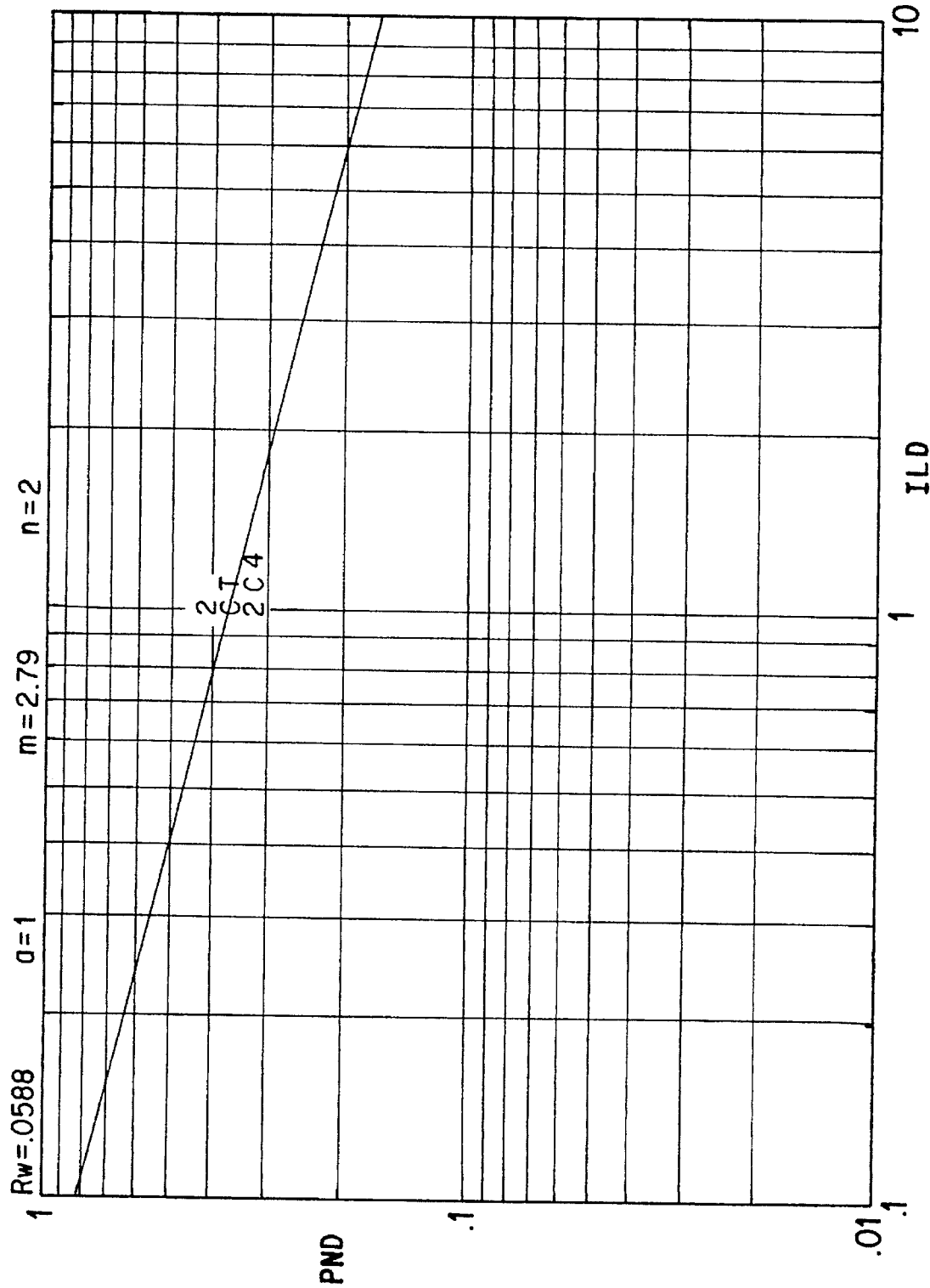
Figure 25A:
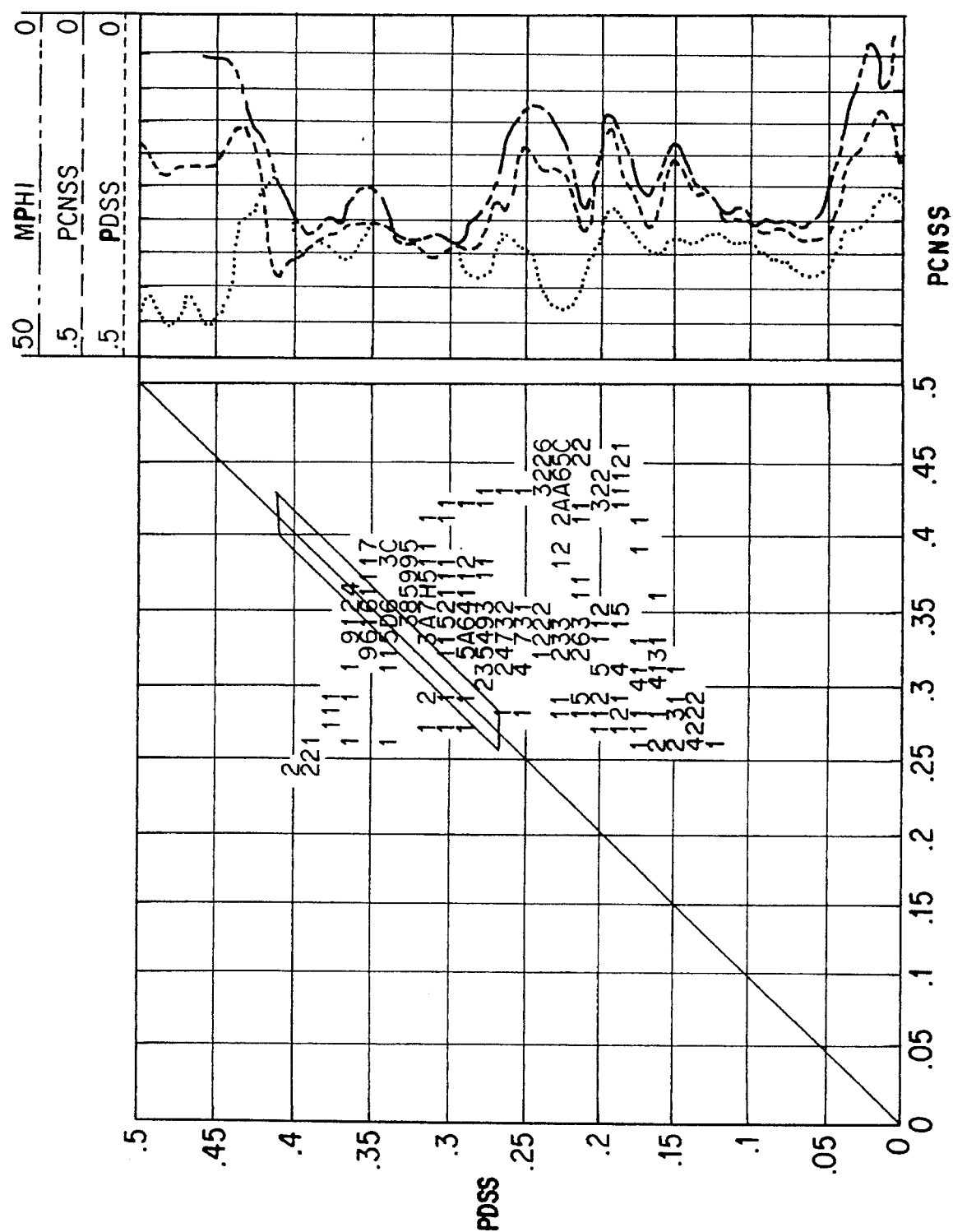
FIG. 25 A is a Density-Neutron Plot with cleanest, wettest sand.
Figure 25B:
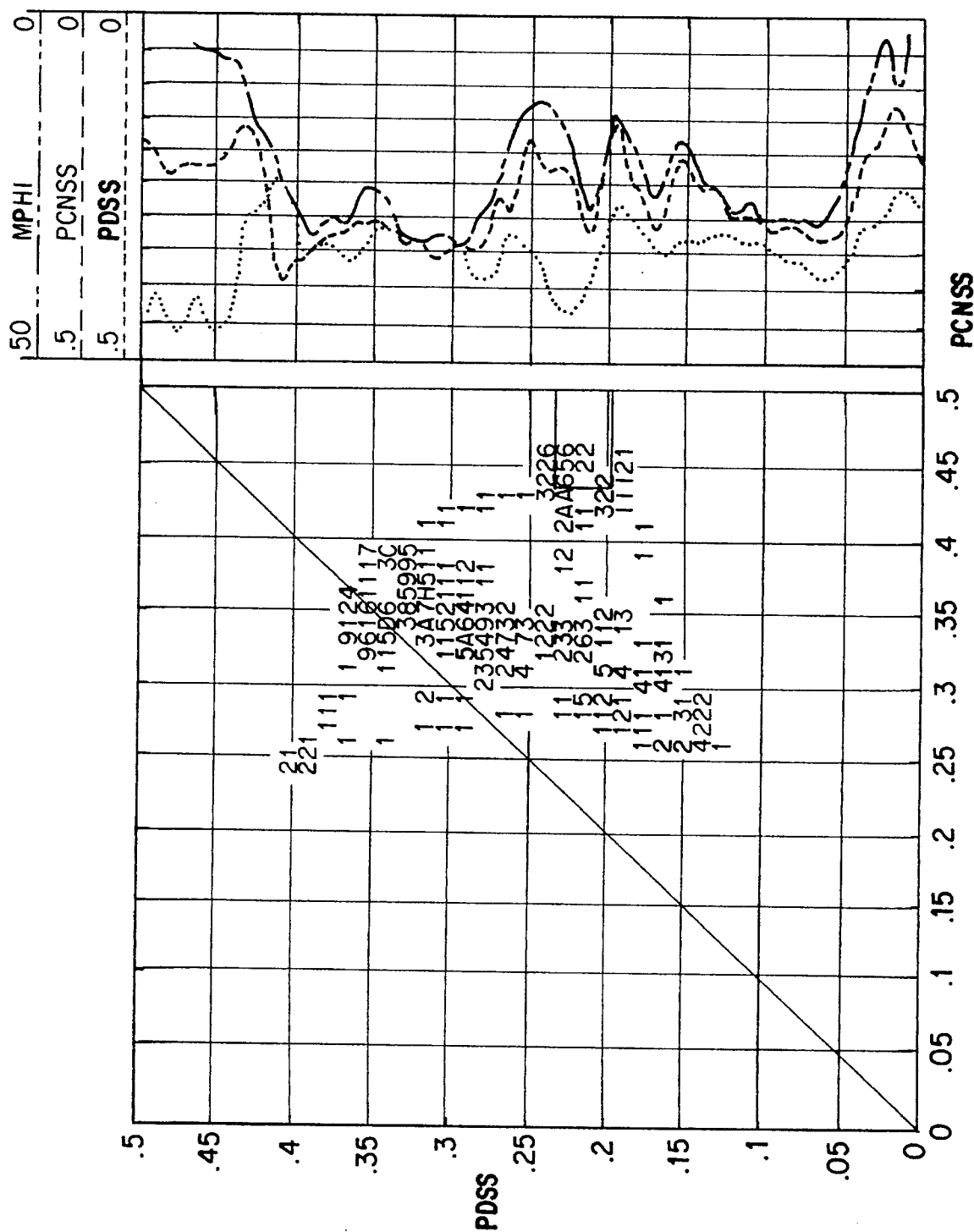

The Pickett plots shown in FIGS. 24A and 24B, where deep resistivity and neutron-density crossplot porosity are plotted on log-log scales, illustrates the relationship between porosity and resistivity for the cleanest sand and the most clay rich shales, respectively. For reference, the plotted intervals are also identified on FIGS. 25A and 25B, which illustrate the density-neutron crossplot.

Pickett plots can be used to determine Rw or, given Rw, to define m assuming a=1. FIG. 24A, the clean sands, is used to determine Rw=0.035 ohm using the typical value a=1. FIG. 24B, the clay-rich shales as defined by the density-neutron shaly sand model, illustrates the apparent m slope needed to fit the data cluster to the given clay water conductivity. Since it is likely that the shale at this depth contains mostly clay bound water, a Swt=1.0 line can be drawn from the Ccw (17 mho/m) (see Eq. 8A above) point through the upper edge of the data cluster. This positioning in the cluster considers that the free formation water conductivity is greater than is that associated with the clay. The slope of this trend line reflects the m exponent of the Archie porosity-formation factor relationship, i.e.:

$$m = \log(Rw/Rt)/\log(PHI_T) \quad (16)$$

The observed slope of 2.79 is much higher than the 1.8 value which is needed in most sands and even higher than the value of 2.00 often imposed in these transforms. While m>1.8 might be expected, m as high as 2.79 is probably unlikely, especially after considering that a porosity error is a much more plausible cause in affecting this slope. This contention seems even more reasonable when the neutron-density crossplot porosity of 36 pu is contrasted to the 23 pu needed for m=2 to apply in this clay rich shale group.

Using a total porosity based on the density log using an assumed matrix density is another approach. In shaly sands, like those of the Gulf Coast area, a quartz grain density of 2.65 g/cc applies well in sands and shales since the clay mineral grain density is close to 2.65 and the shales tend to be a binary mix of these two minerals.

Figure 24C:
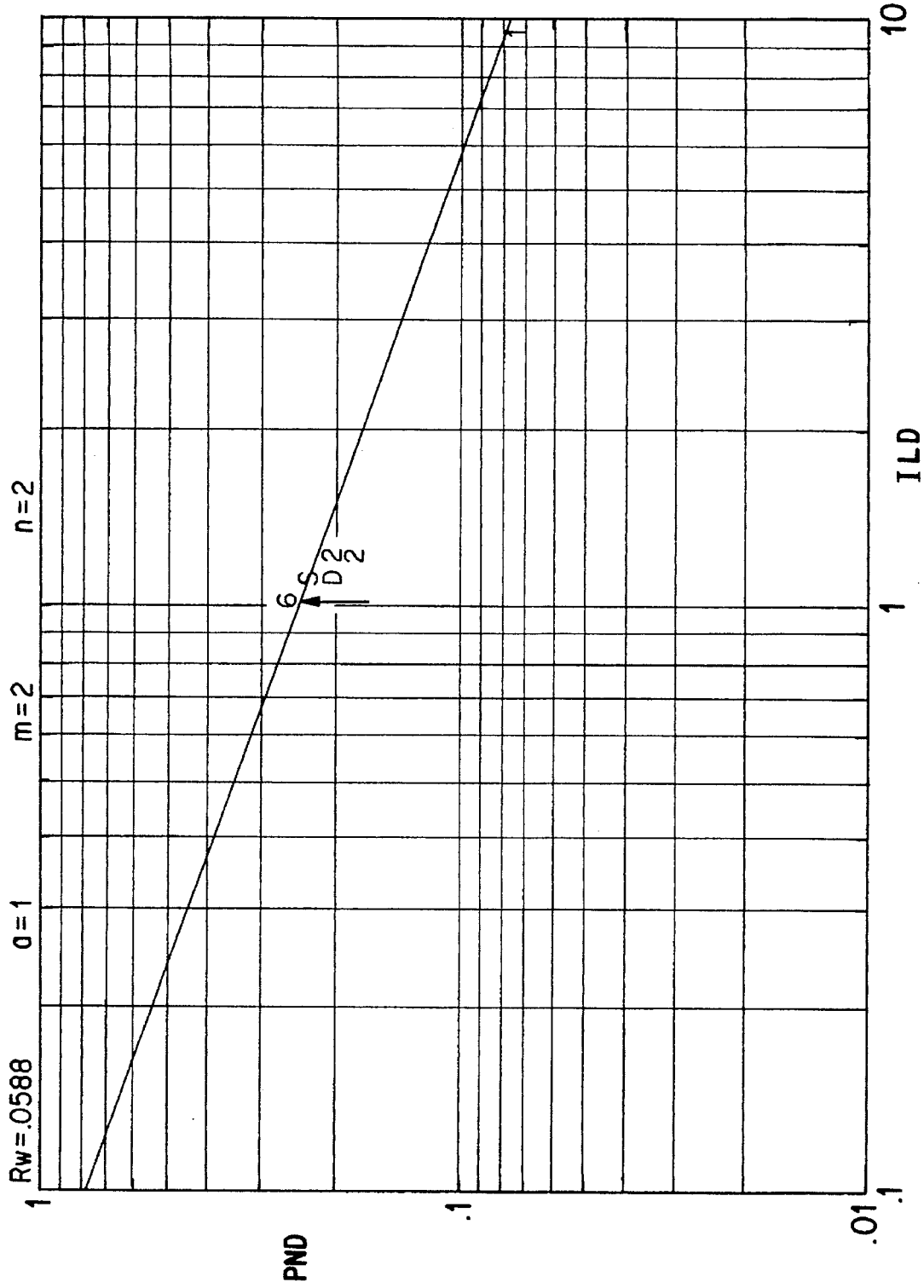

The density porosity method is also favored here because it more closely accommodates the need to match porosity to the Ccw. This is shown in FIG. 24C, a Pickett plot of the same clay rich shale group using density porosity instead of neutron density. The apparent m slope of 2.0 is consistent with other cementation exponent studies and its dependency on clay content.

This process requires the use of a variable exponent to accommodate the sands (m=1.8) and clays (m=2) in the effort to utilize the theoretical clay conductivity parameter Ccw provided by the Dual Water CEC method where clay water conductivity is simply a function of formation temperature when Rw is less than 0.16 ohm, as shown in the expression for the Ccw parameter in Eq. (8A) above.

The variable w approach proposed in 1992 by Coates and Howard, where m and the saturation exponent n are replaced by a single exponent, is useful for this purpose. (Coates, G. R. and Howard, A. D., "Core data and the MRIL show an new approach to formation factor," 33rd Annual Logging Symposium of the Society of Professional Well Log Analysts, Oklahoma City, Okla., Jun. 15, 1992). By integrating the hypothesis that the MRL misses clay porosity within the variable w methodology, a variable exponent is available that varies as a function of the apparent irreducible water saturation of the clean matrix. The functional relationship is shown as Eq. (12) above. In this equation, the final w is held within the boundaries of the wi and ww values calculated from an estimate of total bound water that represents irreducible and water saturated conditions, respectively.

Further Considerations

In practice, it is important to recognize that other factors can impact the application of this approach. Two specific cases are easily recognized; gas in the measurement pore space and micropores associated with either ferromagnetic or paramagnetic materials. Both of these represent situations where the MRL can under-call porosity and result in all over-call in the clay bound water content as defined above. Thus, it is necessary, if this MRL, method is to be systematically applied, that a process be developed that correctly accommodates these events. Two approaches are possible: one that utilizes multiple clay bound water indicators and another that utilizes an iterative process to correctly constrain the clay porosity parameter.

The multiple Swb solution uses the MRL bound water saturation (MSWB) to calibrate the alternate indicators, and, through use of a weighing process, such as the Hodges-Lehmann method, a representative Swb is selected.

The iterative approach, that has been incorporated into a computer processed interpretation package that is diagrammed in FIG. 19 assumes that the MSWB is correct and calculates a total bulk volume of water through a quadratic solution of the Dual-Water equation. Recognizing that the total water volume found should not be less than the total bound water volume, Phicl+MRLBVI, defines a boundary condition that, when Ccw>Cw, allows a progressive reduction in clay bound water volume until the two water volumes balance. When Ccw<Cw, a reduction in clay bound water reduces the resistivity defined water volume and the iteration is bypassed. Any reduction in clay porosity during the iteration is added to the original MRL porosity to allow presentation of a gas/microporosity corrected value.

The block diagram in FIG. 19 is adaptable to using the multiple clay bound water method by assuming that any overcall by MSWB is alleviated by the process of weighted selection.

The execution of the MRIAN methodology provides an apparent conductivity from Eqs. (1) and (14) based on the variable w exponent. This is then used in calculating an apparent Swb from Eq. (15). Comparison of this Swb with that from the original hypothesis, as seen in FIG. 20 where the two Swb approaches tend to coincide in water bearing intervals, offers empirical support that MRL porosity from a 2 ms TE pulse-echo log substantially misses the clay porosity in these shaly sand conditions.

The interpretation results from the Frio series (FIG. 21) as well as the Gulf of Mexico Eugene Island area (FIG. 22) illustrate the application of the MRIAN iterative methodology. These represent but two of the wells interpreted in this manner of the more than 200 that have actually been done. Generally, the m results have been good as judged by production versus prediction. There are, however, areas where the fluid properties have impacted the model, especially in heavy oil (<15 API) and when the total porosity is affected by lithologic variables or washed-out borehole. Consequently, additional investigations are underway to better understand these effects and to investigate in a laboratory the apparent link between Qv and MRIL porosity.

Figure 26A:
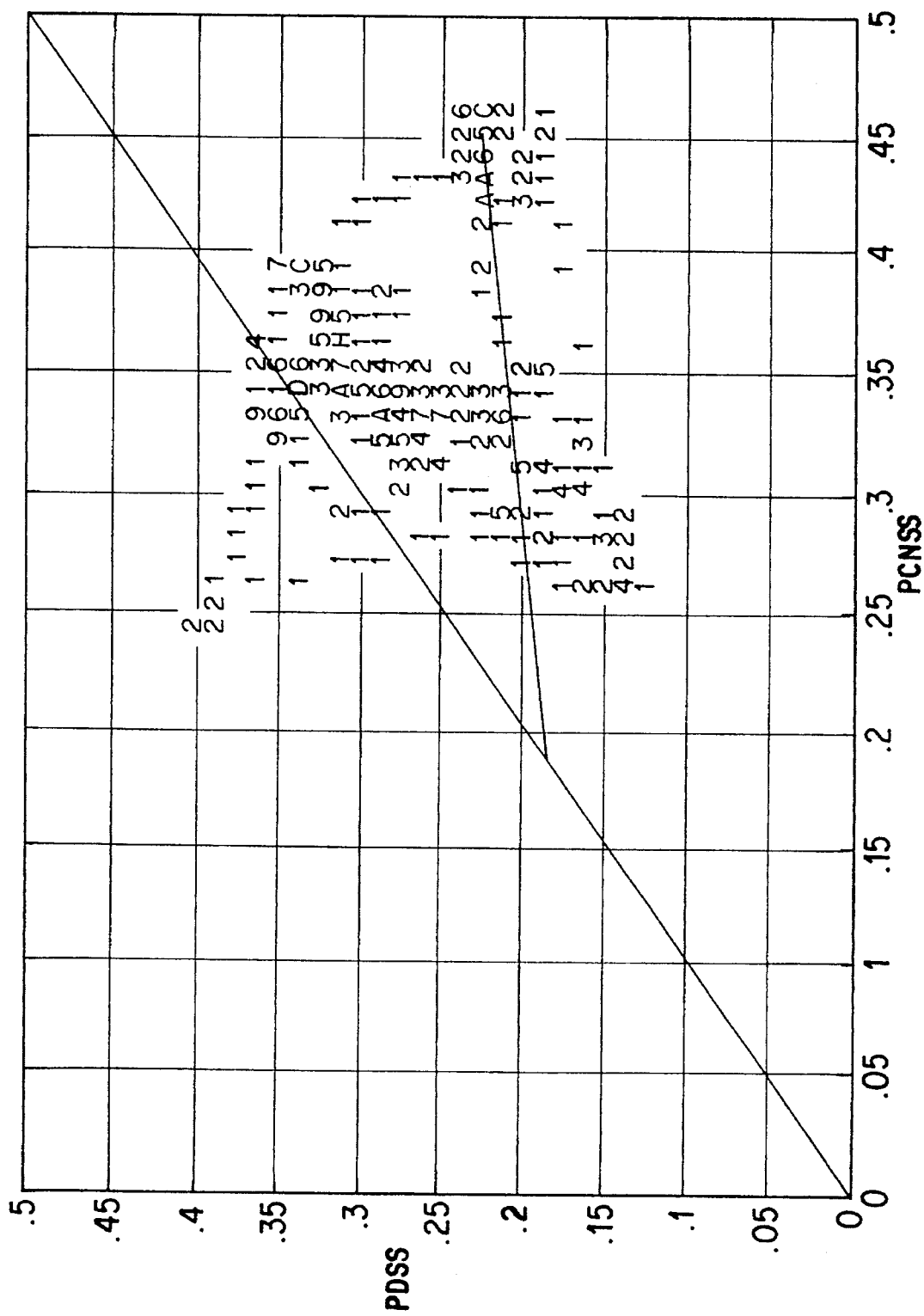
FIG. 26 A is a Density-Neutron plot with total porosity balanced to Ccw.
Figure 26B:
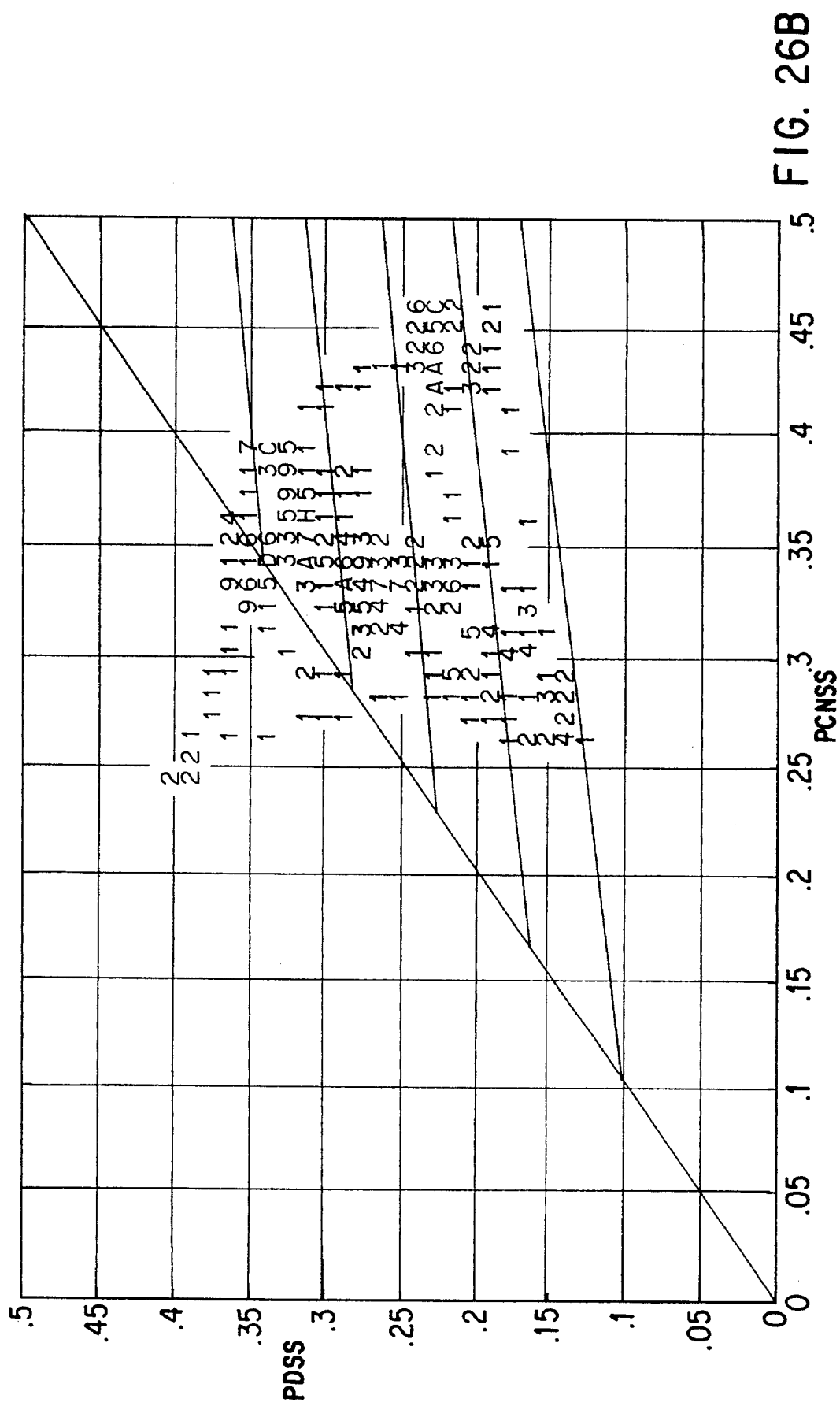
Figure 27:
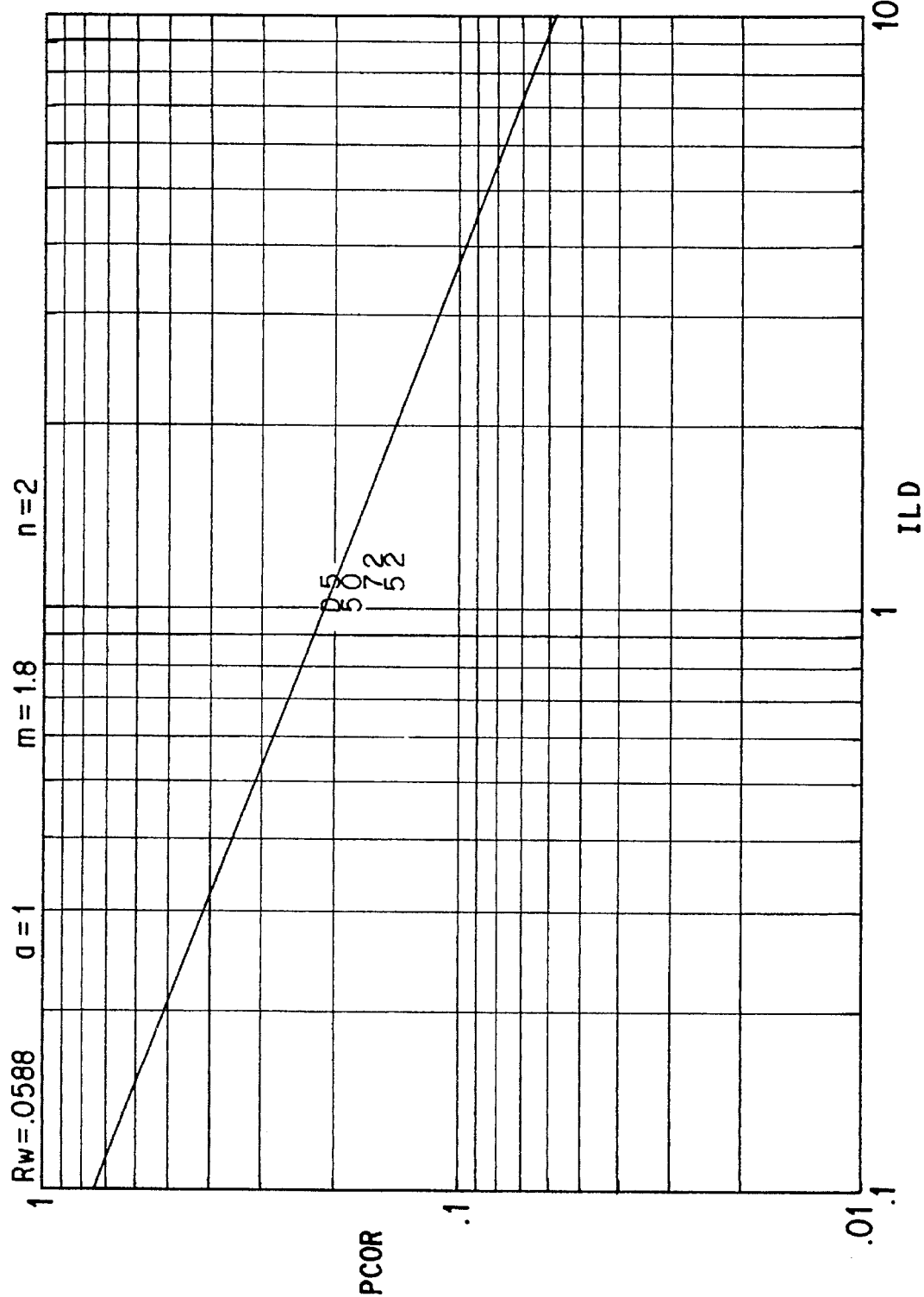
FIG. 27 is a Pickett plot of water example using new total porosity.

FIGS. 26 A–B illustrate a Density-Neutron plot with total porosity balanced to Ccw and total porosity scaling respectively. FIG. 27 is a Pickett plot of water example using new total porosity in accordance with the method of the present invention.

Although the present invention has been described in connection with the preferred embodiment, it is not intended to be limited to the specific form set forth herein, but is intended to cover such modifications, alternatives, and equivalents as can be reasonably included within the spirit and scope of the invention as defined by the following claims.

APPENDIX A

Parameters used in FIG. 19

INPUT CURVES
Phimd—MRL Porosity (Decimal)
Bvimd—MRL Bulk Volume Irreducible (Decimal)
Phiext—External Total Porosity (Decimal)
T—Formation Temperature (Deg. F)
Rt—True Formation Resistivity (Ohm)
INPUT PARAMETERS
Ffimd—MRL Free Fluid Index
Ccw—Clay Water Conductivity
Cw—Free Water Conductivity
Ct—True Formation Conductivity
Swia—Apparent Irreducible Water Saturation
Tbvia—Apparent Total Bulk Volume Irreducible
Swblim—Bound Water Saturation Limit
Swbi—Irreducible Bound Water Saturation
Dcww—Dual Water—Water Conductivity Complex at 100% Water Saturation Conditions
Dcwi—Dual Water—Water Conductivity Complex at Irreducible Water Saturation conditions
Cbvwa—Conventional Bulk Volume Water Apparent
OUTPUT CURVES
Tpor—Total Porosity
Swb—Bound Water Saturation
Clpor—Clay Porosity
Bvit—Bulk Volume Irreducible Total
Ww—Variable W—100% Water Saturation Conditions
Wi—Variable W—Irreducible Water Saturation Conditions
Wq—Variable W
Cbvwt—Conventional Bulk Volume Water total
Cbvwe—Conventional Bulk Volume Water Effective
Pmri—MRIAN Permeability

What is claimed is:

1. A method for determining the composition of a geologic structure, comprising the steps of:

imparting a polarizing magnetic field to a geologic structure for a predetermined period of time;

measuring nuclear magnetic resonance signals representing spin-echo relaxation of a population of particles in the geologic structure;

constructing a chain of spin-echo signals characteristic of said population of particles;

determining values for the magnetic resonance log (MRL) porosity ($PHI_M$) of the geologic structure from said chain of spin-echo signals;

determining values for the total porosity $PHI_t$; and deriving additional petrophysical properties of the geologic structure from the total porosity ($PHI_t$) values and from the MRL porosity ($PHI_M$) values.

2. The method according to claim 1 wherein additional petrophysical properties of the geologic structure are the irreducible bound water saturation, $S_{wb}$, bulk water irreducible fluid volume $BVI_M$ and the bulk-volume water (BVW) of the geologic structure.

3. The method according to claim 2 wherein the value for $S_{wb}$ is determined using the expression:

$$S_{wb}=(PHI_t-PHI_M)/PHI_t.$$

* * * * *